US010856959B2

(12) United States Patent
Chu et al.

(10) Patent No.: US 10,856,959 B2
(45) Date of Patent: Dec. 8, 2020

(54) INSERTION DEVICE FOR DELIVERY OF A MESH CARRIER

(71) Applicant: Boston Scientific Scimed, Inc., Maple Grove, MN (US)

(72) Inventors: Michael S. H. Chu, Brookline, MA (US); Karthik Lavakumar, Framingham, MA (US); Steven A. Olivieri, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 225 days.

(21) Appl. No.: 15/967,004

(22) Filed: Apr. 30, 2018

(65) Prior Publication Data
US 2018/0243066 A1    Aug. 30, 2018

Related U.S. Application Data

(63) Continuation of application No. 14/707,554, filed on May 8, 2015, now Pat. No. 9,974,637, which is a
(Continued)

(51) Int. Cl.
*A61F 2/00* (2006.01)
*A61B 17/04* (2006.01)
(Continued)

(52) U.S. Cl.
CPC ...... *A61F 2/0045* (2013.01); *A61B 17/00234* (2013.01); *A61B 17/0401* (2013.01);
(Continued)

(58) Field of Classification Search
CPC .......... A61B 17/0401; A61B 17/06109; A61B 2017/00805; A61B 2017/0409;
(Continued)

(56) References Cited

U.S. PATENT DOCUMENTS

| 4,840,185 A | 6/1989 | Hernandez |
| 5,059,206 A | 10/1991 | Winters |

(Continued)

FOREIGN PATENT DOCUMENTS

| JP | 2001-511684 A | 8/2001 |
| JP | 2004-500763 A | 1/2004 |

(Continued)

OTHER PUBLICATIONS

International Search Report and Written Opinion for PCT Application No. PCT/US2009/066201, dated Apr. 15, 2010, 19 pages.
(Continued)

*Primary Examiner* — Julian W Woo
(74) *Attorney, Agent, or Firm* — Brake Hughes Bellermann LLP

(57) ABSTRACT

An insertion device includes an elongate member and a stylet. The elongate member has a proximal end portion, a distal end portion, and defines a lumen therethrough. The stylet has a distal end portion, a proximal end portion, and is slidably coupled to the elongate member. The stylet is configured to move from a first position to a second position with respect to the elongate member. The distal end portion of the stylet is configured to removably couple a mesh carrier thereto. A portion of the distal end portion of the stylet is disposed outside of the lumen of the elongate member when the stylet is in its first position and is disposed within the lumen when the stylet is in its second position.

18 Claims, 27 Drawing Sheets

Related U.S. Application Data continuation of application No. 12/623,857, filed on Nov. 23, 2009, now Pat. No. 9,028,509.

(60) Provisional application No. 61/193,542, filed on Dec. 5, 2008.

(51) Int. Cl.
*A61B 17/06* (2006.01)
*A61B 17/00* (2006.01)

(52) U.S. Cl.
CPC ............ *A61B 17/06109* (2013.01); *A61B 2017/00292* (2013.01); *A61B 2017/00805* (2013.01); *A61B 2017/045* (2013.01); *A61B 2017/0409* (2013.01); *A61B 2017/0445* (2013.01); *A61B 2017/0464* (2013.01); *A61F 2220/0008* (2013.01)

(58) Field of Classification Search
CPC ...... A61B 2017/0445; A61B 2017/045; A61B 2017/0464; A61F 2/0045
See application file for complete search history.

(56) References Cited

U.S. PATENT DOCUMENTS

| | | | |
|---|---|---|---|
| 5,433,722 A | 7/1995 | Sharpe et al. | |
| 5,478,353 A | 12/1995 | Yoon | |
| 6,066,146 A | 5/2000 | Carroll et al. | |
| 6,387,041 B1 | 5/2002 | Harari et al. | |
| 7,056,333 B2 * | 6/2006 | Walshe | A61B 17/0401 606/232 |
| 7,387,634 B2 | 6/2008 | Benderev et al. | |
| 7,527,588 B2 * | 5/2009 | Zaddem | A61B 17/06109 600/29 |
| 8,192,458 B2 | 6/2012 | Hart et al. | |
| 8,944,990 B2 * | 2/2015 | Hamel | A61B 17/06109 600/37 |
| 9,028,509 B2 * | 5/2015 | Chu | A61F 2/0045 606/139 |
| 9,301,750 B2 * | 4/2016 | Ostrovsky | A61B 17/06109 |
| 10,716,556 B2 * | 7/2020 | ElAttrache | A61F 2/0811 |
| 2002/0013608 A1 | 1/2002 | Elattrache et al. | |
| 2002/0193830 A1 | 12/2002 | Bonutti | |
| 2003/0105489 A1 | 6/2003 | Eichhorn et al. | |
| 2003/0176762 A1 | 9/2003 | Ciamporcero et al. | |
| 2004/0087970 A1 | 5/2004 | Chu et al. | |
| 2006/0089525 A1 | 4/2006 | Mamo et al. | |
| 2006/0167481 A1 | 7/2006 | Baker et al. | |
| 2006/0173468 A1 | 8/2006 | Simmon et al. | |
| 2010/0145368 A1 | 6/2010 | Chu et al. | |
| 2015/0238298 A1 | 8/2015 | Chu et al. | |

FOREIGN PATENT DOCUMENTS

| | | |
|---|---|---|
| JP | 2006-502754 A | 1/2006 |
| JP | 2010-540020 A | 12/2010 |
| WO | 2007/016698 A2 | 2/2007 |
| WO | 2007/149348 A2 | 12/2007 |
| WO | 2009/038781 A1 | 3/2009 |
| WO | 2010/065504 A1 | 6/2010 |

OTHER PUBLICATIONS

International Preliminary Report on Patentability for PCT Application No. PCT/US2009/066201, dated Jun. 16, 2011, 11 pages.
Office action for Australian Patent Application No. 2009322595, dated Feb. 12, 2014, 5 pages.
Response to Office action for Australian Patent Application No. 2009322595, filed on Feb. 12, 2015, 19 pages.
Office action for Japanese Patent Application No. 2011-539628, dated Jul. 7, 2014, 2 pages.
Response to Office Action for Japanese Patent Application No. 2011-539628, filed on Oct. 7, 2014, 3 pages.
Office Action for JP Application No. 2014-55754, dated Mar. 9, 2015, 1 page.
Notice of Allowance for Japanese Patent Application No. 2011-539628, dated Feb. 13, 2015, 3 pages.
Notice of Allowance for Canadian Application No. 2,745,458, dated Aug. 25, 2016, 1 page.
Notice of Acceptance for AU Application No. 2009322595, dated Oct. 7, 2015, 2 pages.
Response to Second Examiner Report for AU Application No. 2009322595, filed Sep. 28, 2015, 14 pages.
Second Examiner Report for AU Application No. 2009322595, dated Apr. 30, 2015, 3 pages.
Office Action for CA Application No. 2,745,458, dated Oct. 23, 2015, 5 pages.
Office Action Response for CA Application No. 2,745,458, filed Apr. 22, 2016, 15 pages.
Office Action for JP Application No. 2014-55754, dated Oct. 21, 2015, 3 pages.
Office Action Response for JP Application No. 2014-55754, filed Jan. 21, 2016, 10 pages.
Office Action Response for JP Application No. 2014-55754, filed Jun. 9, 2015, 12 pages.

* cited by examiner

INSERTION DEVICE FOR DELIVERY OF A MESH CARRIER

CROSS-REFERENCE TO RELATED APPLICATIONS

This application is a Continuation of, and claims priority to, U.S. patent application Ser. No. 14/707,554, filed on May 8, 2015, entitled "INSERTION DEVICE FOR DELIVERY OF A MESH CARRIER", which is a continuation of, and claims priority to, U.S. patent application Ser. No. 12/623,857, filed on Nov. 23, 2009, entitled "INSERTION DEVICE AND METHOD FOR DELIVERY OF A MESH CARRIER", which, in turn, claims priority to U.S. Patent Application No. 61/193,542, filed on Dec. 5, 2008, entitled "INSERTION DEVICE AND METHOD FOR DELIVERY OF A MESH CARRIER", the disclosures of which are incorporated by reference herein in their entirety.

BACKGROUND

The disclosed embodiments relate generally to medical devices and more particularly to an insertion device for delivery of a mesh carrier into a body of a patient.

The disclosed embodiments have application to a wide variety of surgical procedures. For example, one such procedure is directed to urinary incontinence and includes fixing an implant to tissue within a body of a patient to provide support for the urethra. Another such procedure includes fixing an implant to bodily tissue of a patient to support a bladder of the patient.

Mesh carriers may be placed within a body of a patient to provide anchoring points for medical implants. In some procedures, it is necessary for a practitioner, such as a physician, to insert a mesh carrier into bodily tissue of the patient at a location not easily visible to the practitioner. In such procedures, known insertion devices can be used to position a mesh carrier at a first location within bodily tissue and to fix the mesh carrier to the tissue. However, when the mesh carrier is removed from the insertion device, the mesh carrier may be fixed to the tissue at a second location different from the first location. For example, when the mesh carrier is removed from the insertion device, it can be pushed to a location deeper within the tissue than its location when first inserted. In such an instance, over-insertion can occur resulting in misplacement of the mesh carrier. If misplacement of the mesh carrier occurs, the practitioner may remove or pull out the misplaced mesh carrier or implant, which can cause severe or unnecessary trauma to the patient.

Thus, a need exists for an insertion device having a configuration that permits the mesh carrier to remain at a single location within bodily tissue once the mesh carrier has been inserted into the tissue and during removal from the insertion device. A need also exists for an insertion device having a configuration that facilitates deployment of the mesh carrier from the insertion device.

SUMMARY

In some embodiments, an insertion device includes an elongate member and a stylet. The elongate member has a proximal end portion, a distal end portion, and defines a lumen between the proximal end portion and the distal end portion. The stylet has a distal end portion and a proximal end portion. The stylet is slidably coupled to the elongate member such that the stylet is configured to move from a first position to a second position with respect to the elongate member. The distal end portion of the stylet is configured to removably couple a mesh carrier thereto. A portion of the distal end portion of the stylet is disposed outside of the lumen of the elongate member when the stylet is in its first position and is disposed within the lumen when the stylet is in its second position.

In other embodiments, the elongate member includes a proximal end portion, a distal end portion, and defines a lumen therethrough. The stylet has a distal end portion and a proximal end portion, and is configured to move from a first position to a second position. The distal end portion of the stylet is configured to removably couple a mesh carrier thereto and is configured to be coupled to the mesh carrier when the stylet is in its first position. The elongate member is configured to contact the mesh carrier and decouple the mesh carrier from the distal end portion of the stylet in response to the stylet moving from its first position to its second position.

DETAILED DESCRIPTION

The insertion device and mesh carrier described herein can be inserted into a body of a patient, such as into bodily tissue. For example, the insertion device can be configured to deliver a first mesh carrier configured to selectively retain an implant (also referred to herein as a "filament", "tape", "implant", "mesh", "sling", or "strap") with respect to bodily tissue. A plurality of such mesh carriers can be anchored within the body of a patient at spaced locations while retaining a filament between the plurality of mesh carriers to provide support for other portions of the body (e.g., organs or portions of organs).

The insertion device is configured to place, deposit, or otherwise insert a mesh carrier into a bodily tissue of a patient. The filament is configured to suspend or support a bodily tissue or organ when the filament is retained within the patient by one mesh carrier. Thus, in one embodiment, the insertion device can place the mesh carrier into the obturator extemus muscle for incontinence treatment. Specifically, first and second mesh carriers are placed in the obturator extemus muscle of a patient and the filament is extended between the first and second mesh carriers to support the urethra or bladder neck of the patient. The insertion device can be a variety of different configurations and can have a variety of different components.

As used in this specification, the words "proximal" and "distal" refer to the direction closer to and further away from, respectively, an operator (e.g., surgeon, physician, nurse, technician, etc.) who would use an insertion device or a therapeutic device during a procedure. For example, the end of an insertion device first to contact the patient's body would be the distal end, while the opposite end of the insertion device (e.g., the end of the insertion device being operated by the operator) would be the proximal end of the insertion device. Similarly, the end of a insertion device implanted the furthest within the patient's body would be the distal end, while the opposite end of the insertion device (e.g., the end of the insertion device that is implanted the least amount within the body or the end of the insertion device that is disposed outside of the body) would be the proximal end.

Figure 1:
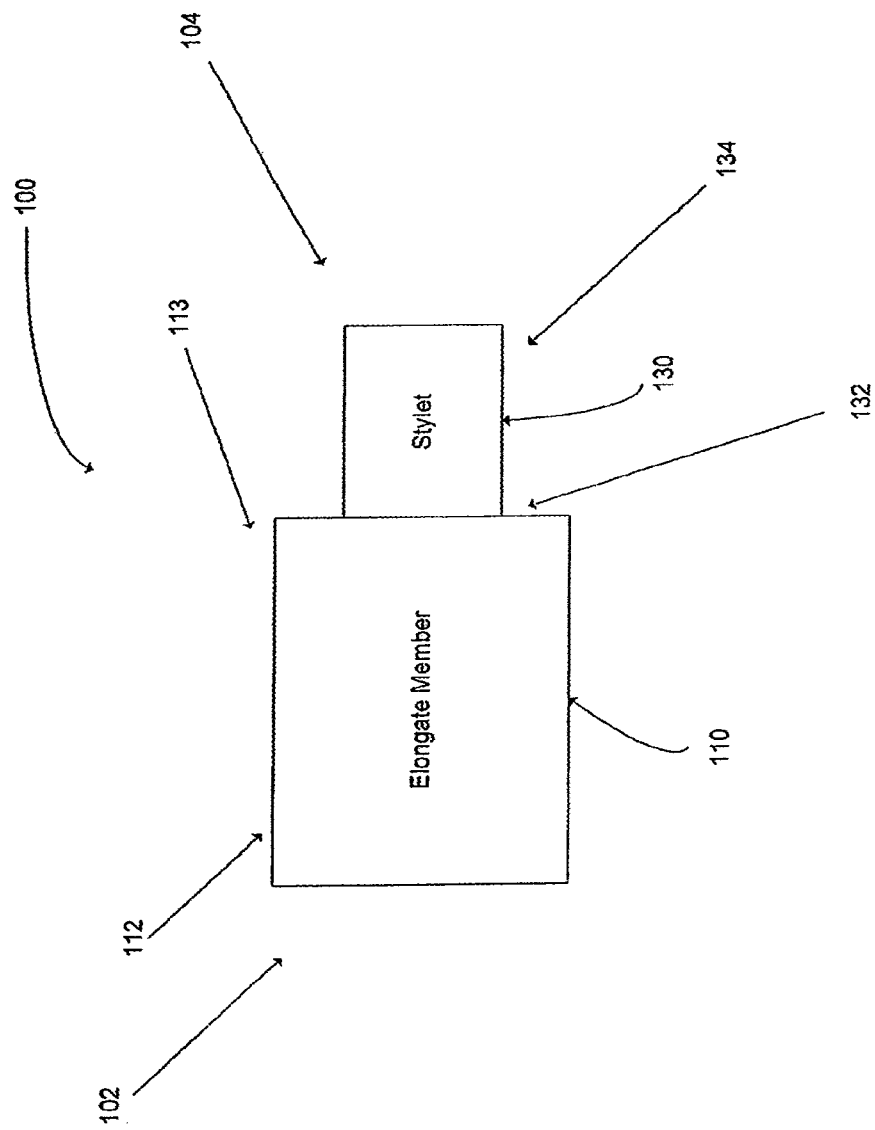
FIG. 1 is a schematic illustration of an insertion device according to one embodiment.

FIG. 1 is a schematic illustration of an insertion device 100 according to an embodiment of the invention. The insertion device 100 can be inserted into a body of a patient, such as into bodily tissue.

The insertion device 100 has a proximal end portion 102 and a distal end portion 104. The insertion device 100 includes an elongate member 110 and a stylet 130. At least a portion of the elongate member 110 and a portion of the stylet 130 are configured to be inserted into a body of a patient. The elongate member 110 includes a proximal end portion 112 and a distal end portion 113 and is configured to move with respect to the stylet 130.

The stylet 130, in some embodiments, includes a proximal end portion 132 and a distal end portion 134. The distal end portion 134 is configured to interact with a mesh carrier. The stylet 130 is configured to move with respect to the elongate member 110 from a first position to a second position.

When the stylet 130 is in its first position, a portion of the distal end portion 134 of the stylet 130 extends beyond the distal end portion 113 of the elongate member 110, and is configured to be coupled to the mesh carrier. As the stylet 130 is moved proximally from its first position to its second position, the distal end portion 113 of the elongate member 110 contacts the mesh carrier preventing further proximal movement of the mesh carrier. When the stylet 130 is in its second position, the portion of the distal end portion 134 of the stylet 130, which extended beyond the distal end portion 113 of the elongate member 110 when the stylet 130 was in its first position, is disposed within a lumen of the elongate member 110. Thus, as the stylet 130 is moved from its first position to its second position, the mesh carrier is decoupled or removed from the distal end portion 134 of the stylet 130 and is released in bodily tissue.

In some embodiments, the elongate member defines a lumen extending between the proximal end portion and the distal end portion. In such an embodiment, the lumen is configured to receive the stylet.

In some embodiments, the proximal end portion of the stylet can be configured to be coupled to a handle.

Although a mesh carrier is used with insertion device 100 as described in the above disclosed embodiment, it should be understood that in some embodiments, a tissue anchor can be used.

FIGS. 2-16 and 20 illustrate one embodiment an insertion device. Insertion device 200 has a proximal end portion 202 and a distal end portion 204 (which includes a portion of both an elongate member 210 and a stylet 230). The elongate member 210 and stylet 230 are configured to be at least partially inserted into a body of a patient.

The elongate member 210 includes a proximal end portion 212 and a distal end portion 213, and defines a lumen 218 (shown, for example, in FIG. 13) that extends between the proximal end portion 212 and the distal end portion 213 and is configured to receive at least a portion of the stylet 230. In the illustrated embodiment, the elongate member 210 of the insertion device 200 comprises a substantially flexible material, thereby permitting the elongate member 210 to conform to the shape of the stylet 200.

Figure 4A:
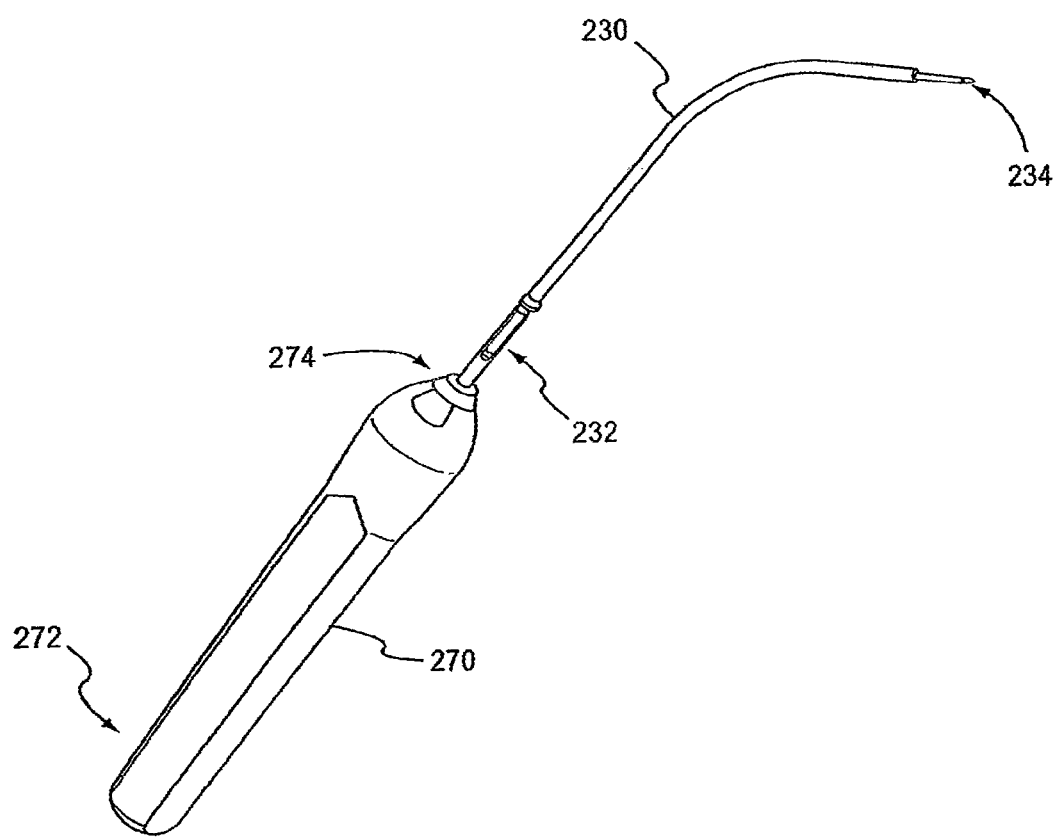
FIG. 4a is a perspective view of the stylet of the insertion device of FIG. 2.
Figure 4B:
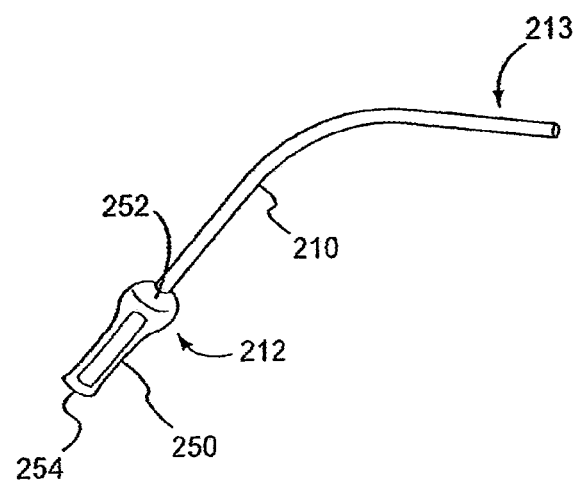
FIG. 4b is a perspective view of the elongate member of the insertion device of FIG. 2.
Figure 5:
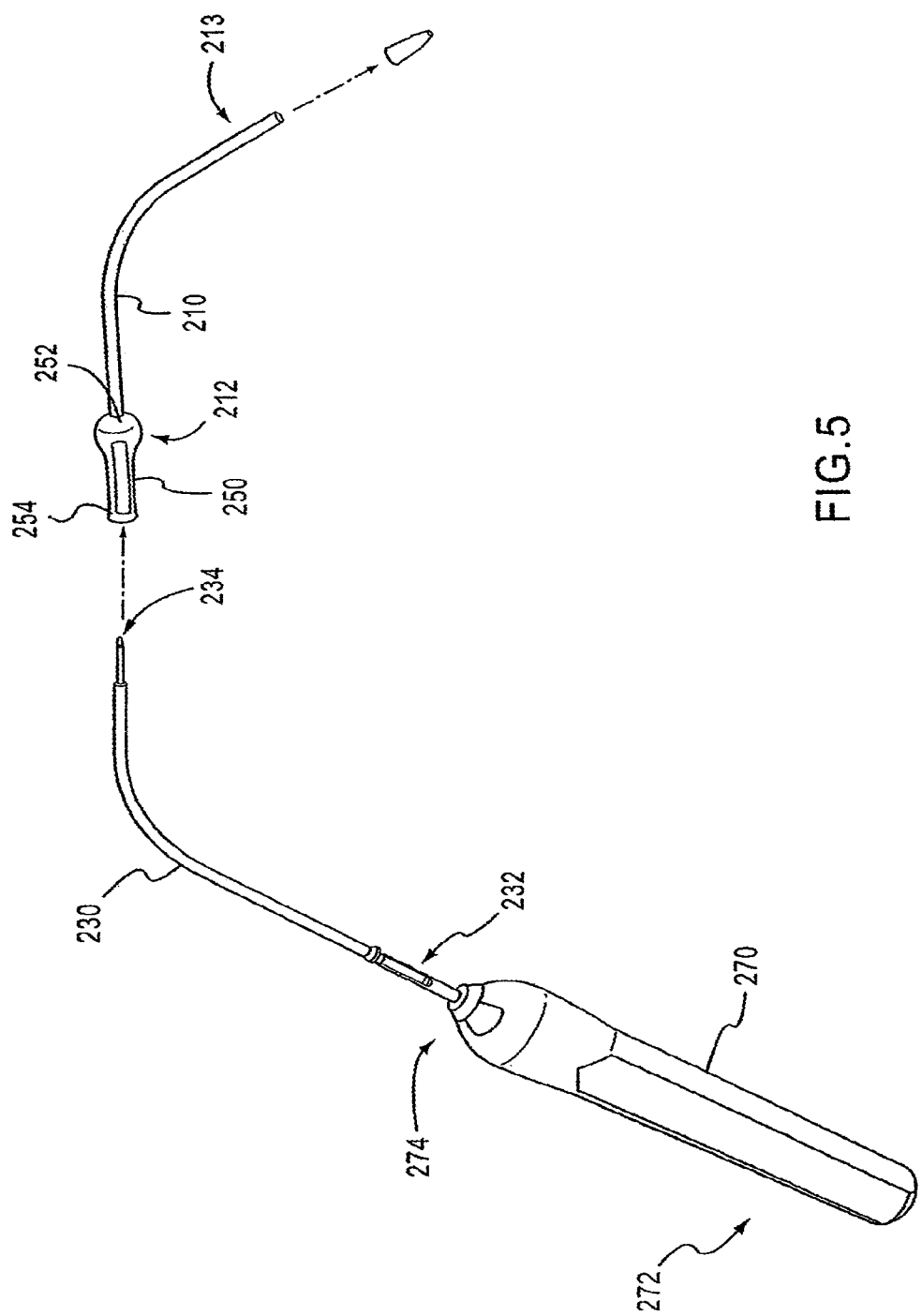
FIG. 5 is an exploded view of the insertion device of FIG. 2 and a mesh carrier.
Figure 6:
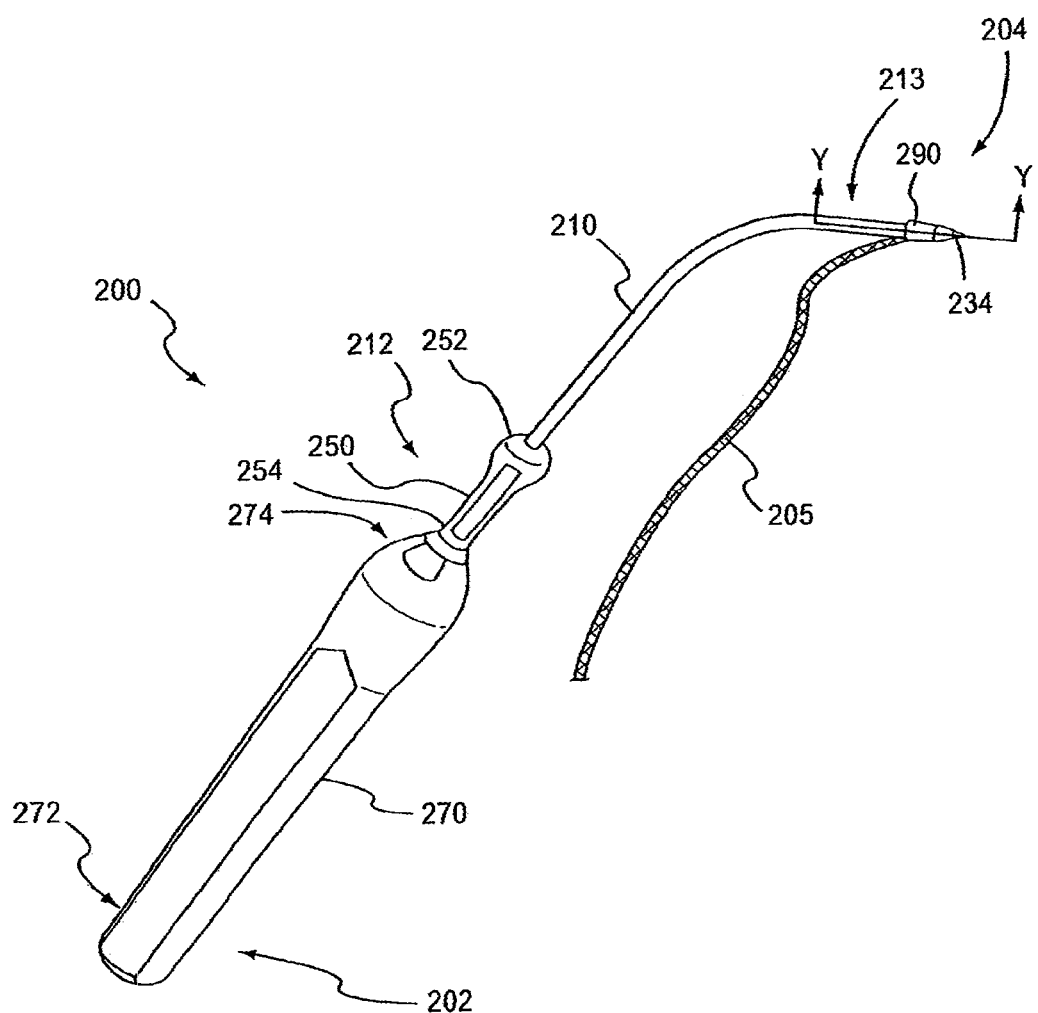
FIG. 6 is a perspective view the insertion device of FIG. 2 coupled to a mesh carrier and filament.
Figure 7:
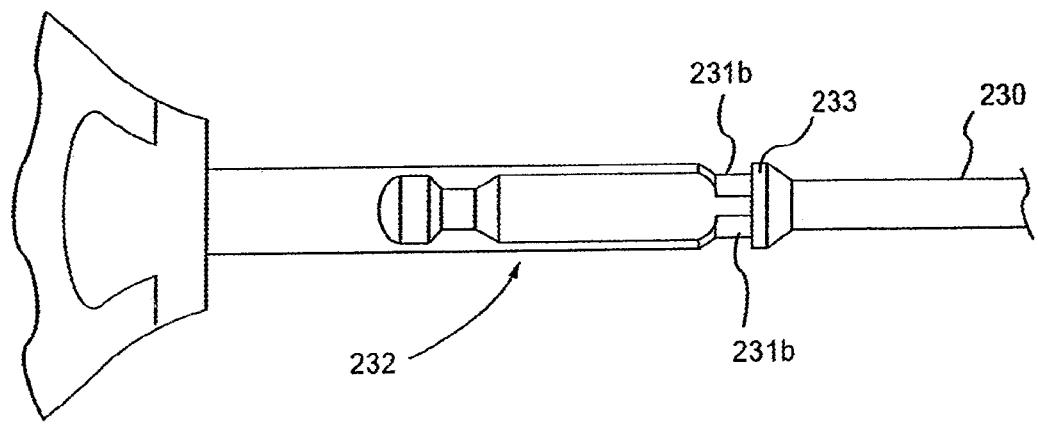
FIG. 7 is a side view of a portion of the stylet of the insertion device of FIG. 2.
Figure 8:
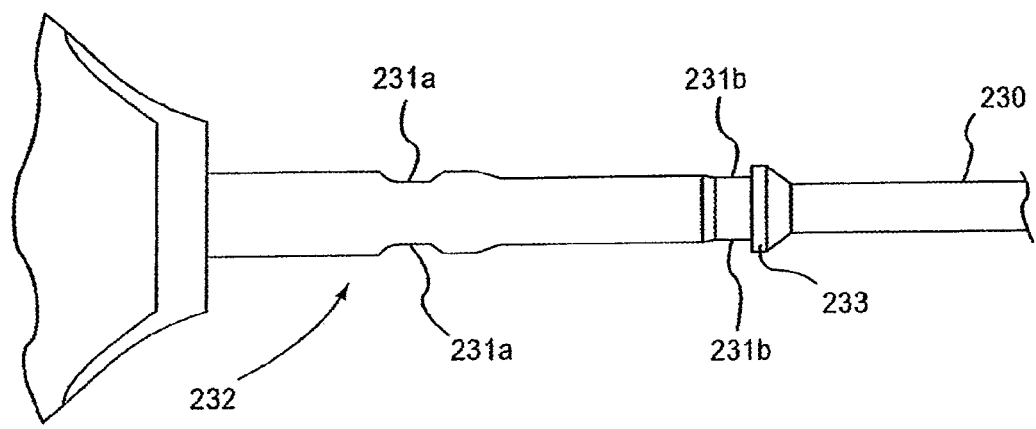
FIG. 8 is a top view of a portion of the stylet of the insertion device of FIG. 2.
Figure 9:
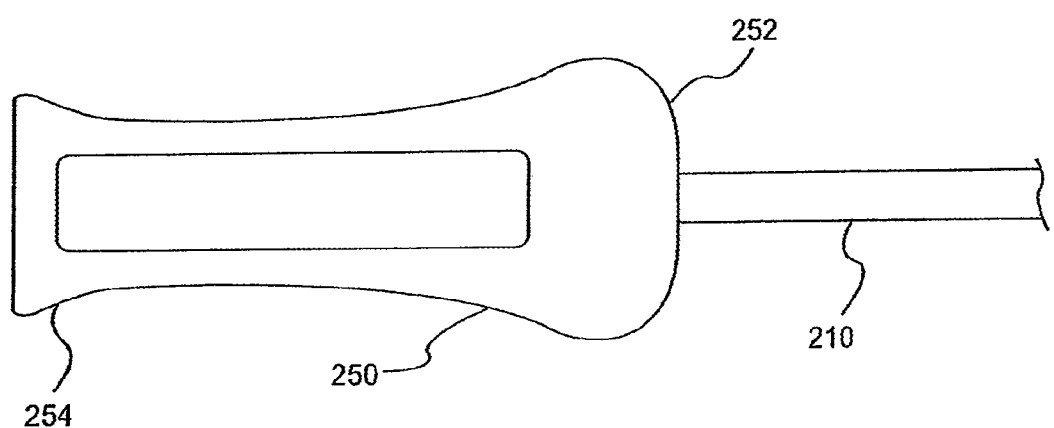
FIG. 9 is a side view of a portion of the elongate member of the insertion device of FIG. 2.
Figure 10:
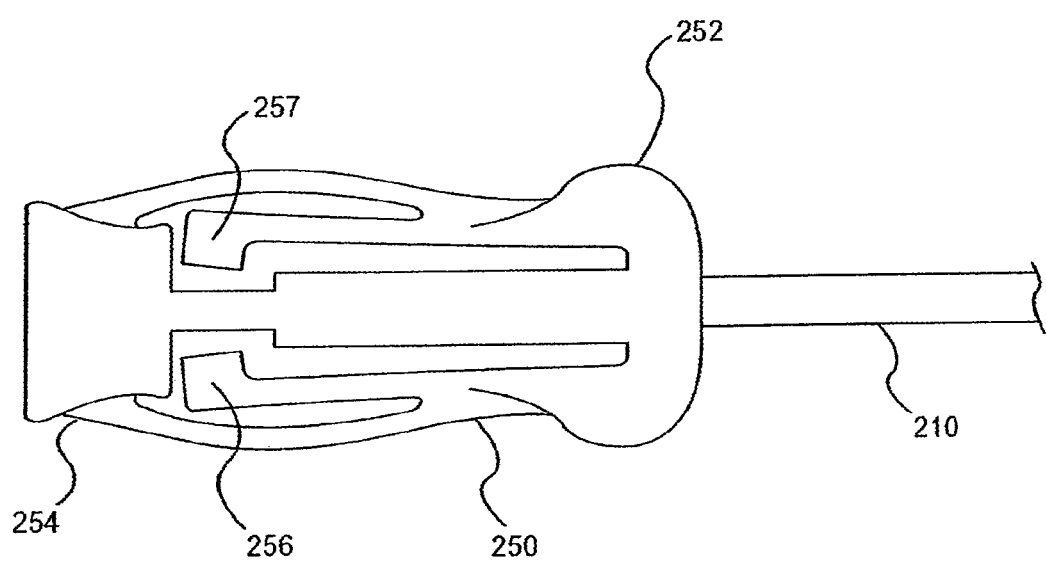
FIG. 10 is a top view of a portion of an elongate member of the insertion device of FIG. 2.
Figure 11:
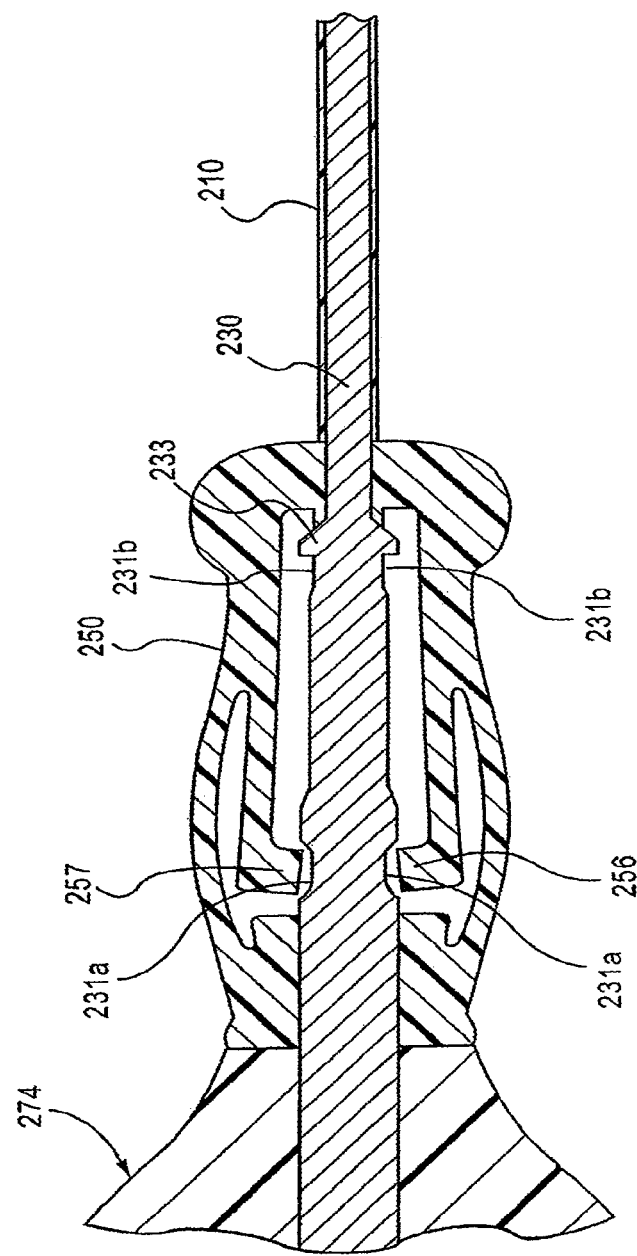
FIG. 11 is a cross-sectional view of a portion of the insertion device of FIG. 2 in its first position.

As shown in FIGS. 4b, 9, and 10, the elongate member 210 includes a base member 250 coupled to its proximal end portion 212. The base member 250 includes a distal end portion 252, a proximal end portion 254, and further defines a portion of the lumen 218 of the elongate member 210. Specifically, the base member 250 is configured to be disposed around or to be slidably coupled to at least a portion of the stylet 230 (described in more detail below). The distal end portion 252 is configured to be fixedly coupled to the proximal end portion 212 of the elongate member 210. The distal end portion 252 of the base member 250 can be fixedly coupled to the elongate member 210 by any suitable coupling mechanism. For example, in some embodiments, the base member 250 and the elongate member 210 can be monolithically constructed.

Figure 2:
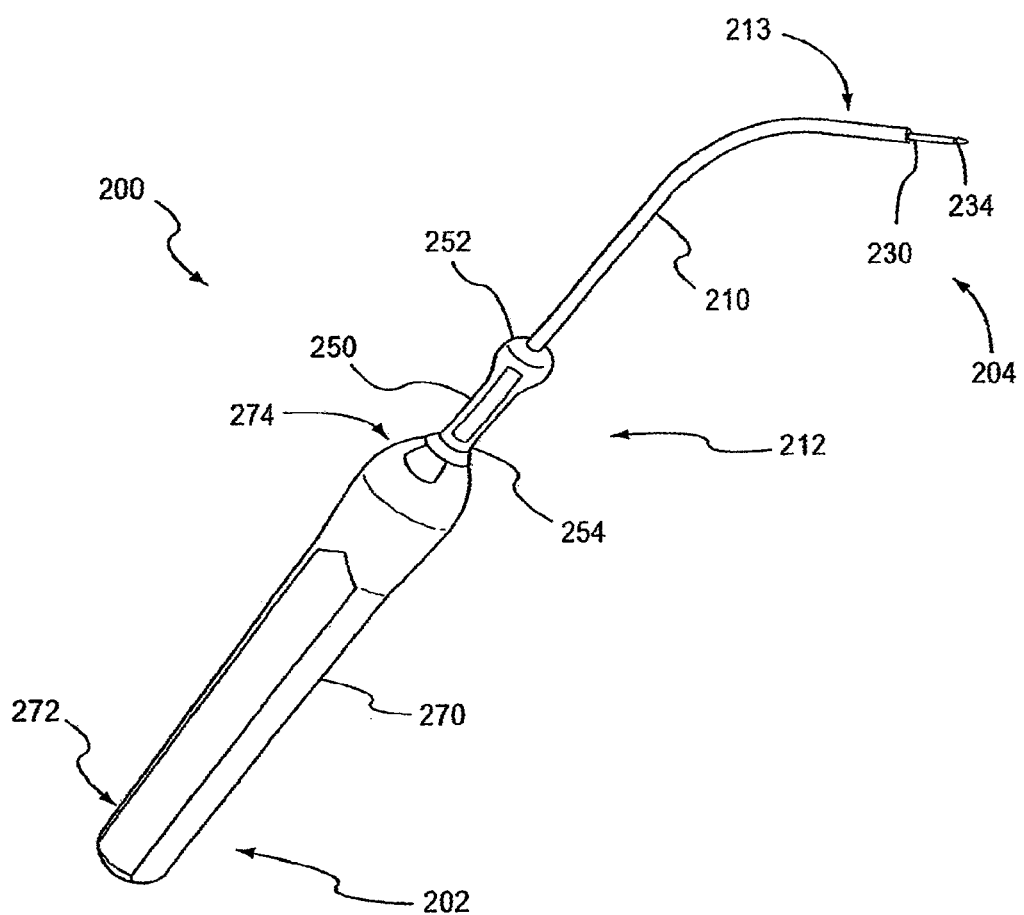
FIG. 2 is a perspective view of an insertion device with a stylet in a first position according to another embodiment.
Figure 3:
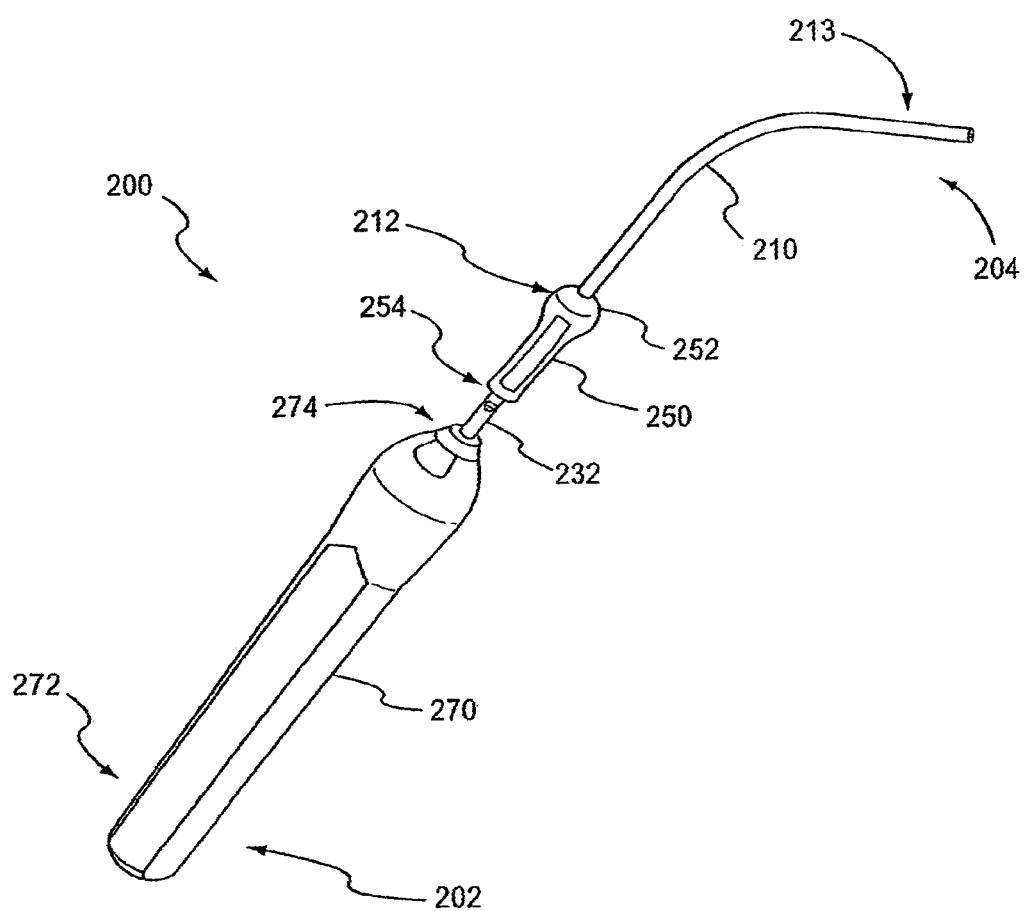
FIG. 3 is a perspective view of the insertion device of FIG. 2 with the stylet in a second position.
Figure 12:
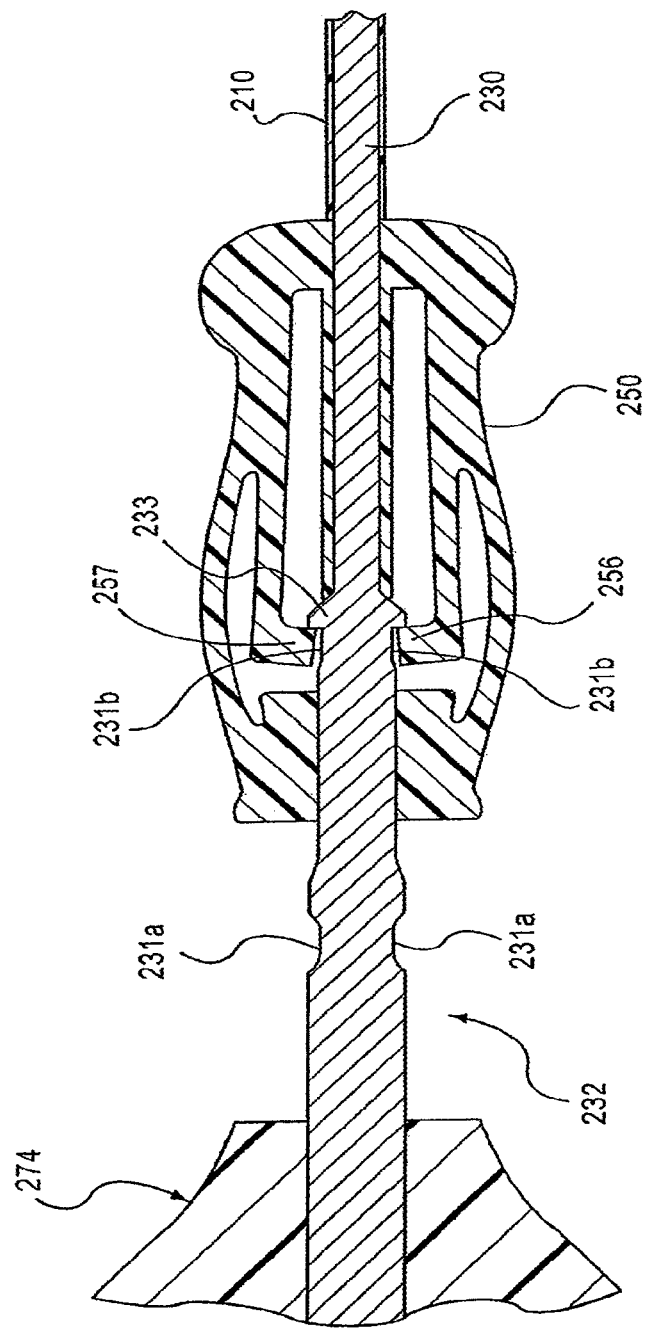
FIG. 12 is a cross-sectional view of a portion of the insertion device of FIG. 2 in its second position.

The proximal end portion 254 of the base member 250 is configured to be disposed proximate a distal end portion 274 of a handle 270 when the stylet 230 is in a first position (shown, for example, in FIGS. 2 and 11) and is configured to be spaced apart from the distal end portion 274 of the handle 270 when the stylet 230 is in a second position (shown, for example in FIGS. 3 and 12). In the illustrated embodiment, the base member 250 is disposed on and is slidably coupled to a proximal end portion 232 of the stylet 230.

In the illustrated embodiment, the base member 250 includes projections 256 and 257 extending therefrom, (shown in FIGS. 10-12) for preventing excessive proximal or distal movement of the elongate member relative to the stylet 230 (discussed in more detail herein). The base member 250 can be constructed of any suitable material. In one embodiment, the base member 250 can be constructed of a polymer. For example, the base member 250 can be constructed of acrylonitrile butadiene styrene (ABS).

Figure 13:
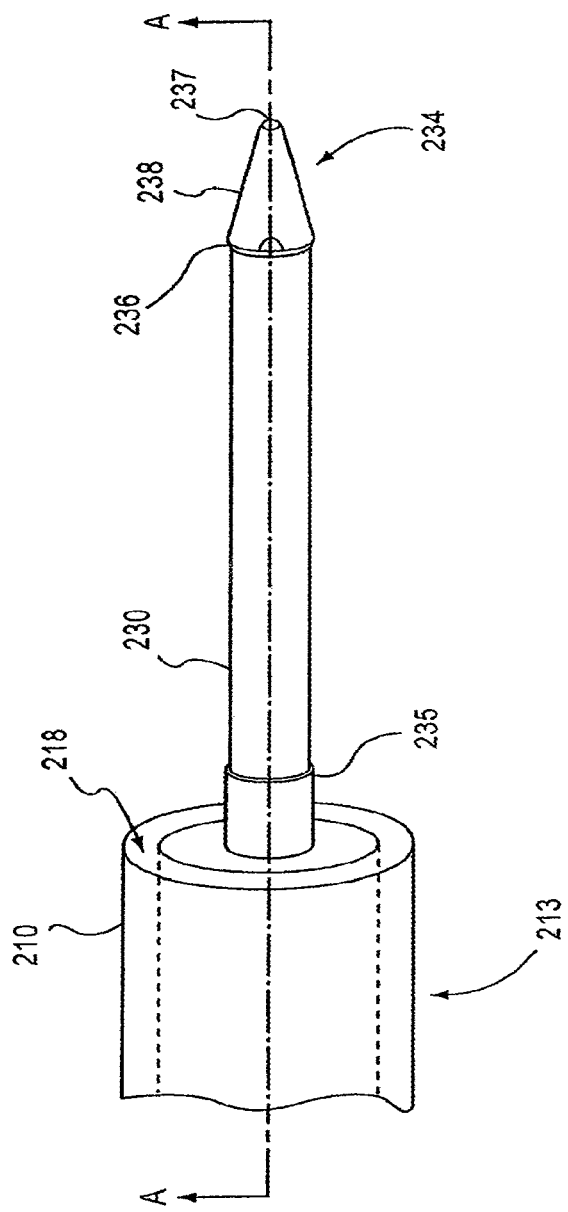
FIG. 13 is a side view of a distal end portion of the insertion device of FIG. 2.
Figure 14:
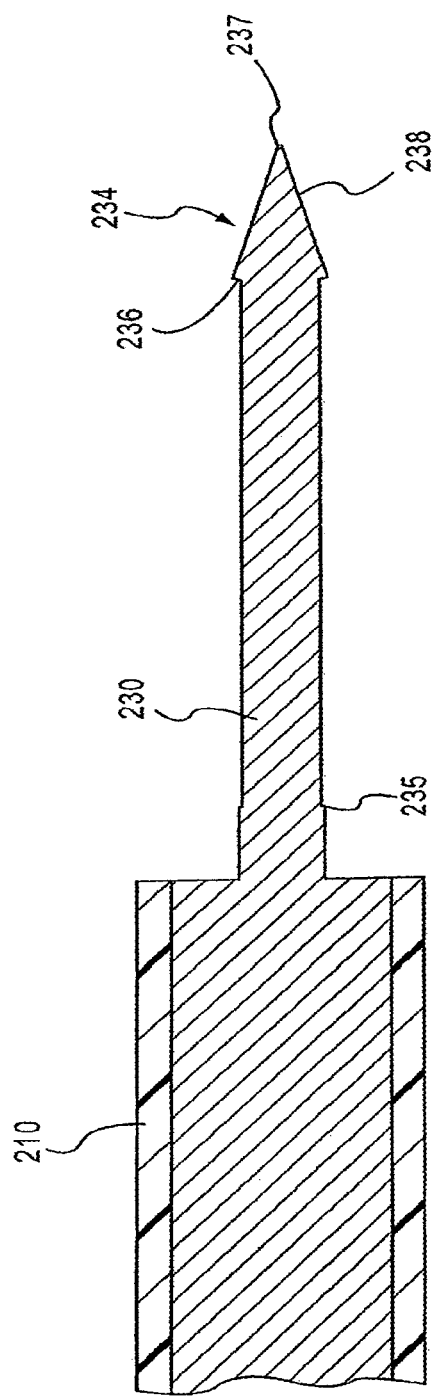
FIG. 14 is a cross-section view of the distal end portion taken along line A-A of FIG. 13.
Figure 15A:
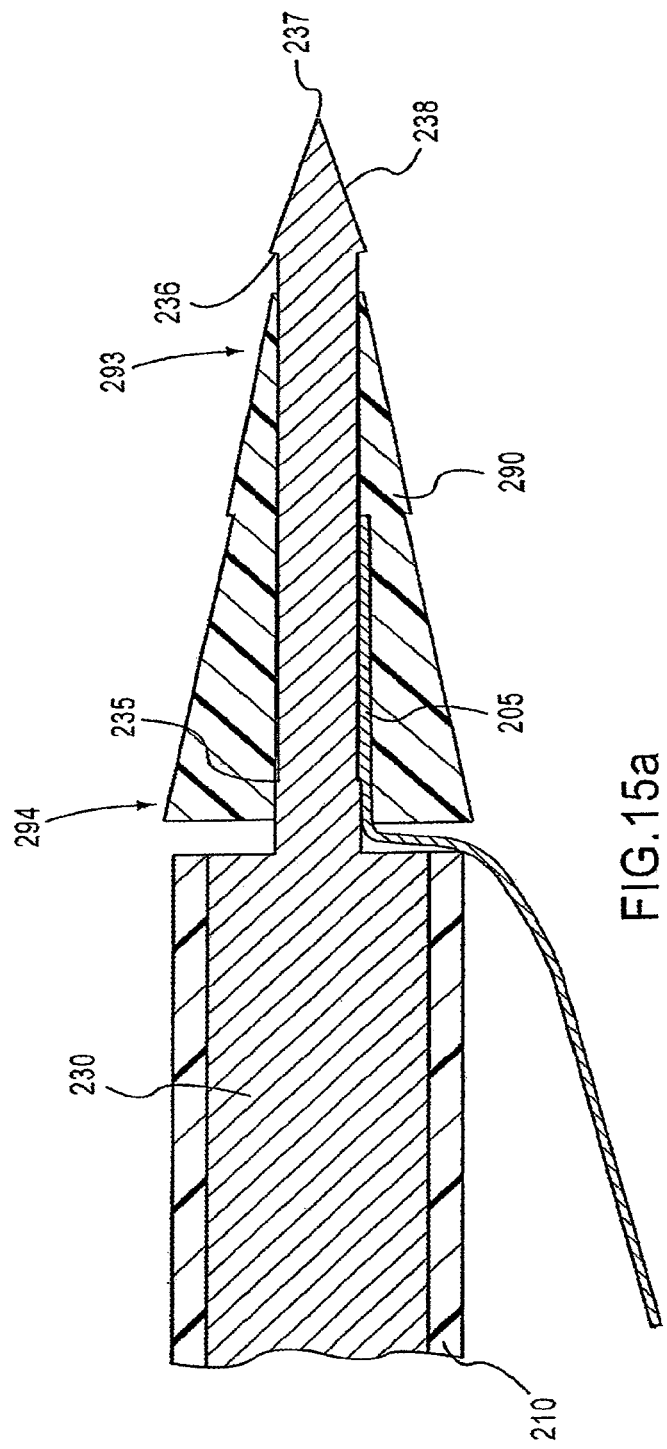
FIGS. 15a and 15b are cross-sectional views of a distal end portion of the insertion device of FIG. 6 in a first position along line Y-Y of FIG. 6.
Figure 15B:
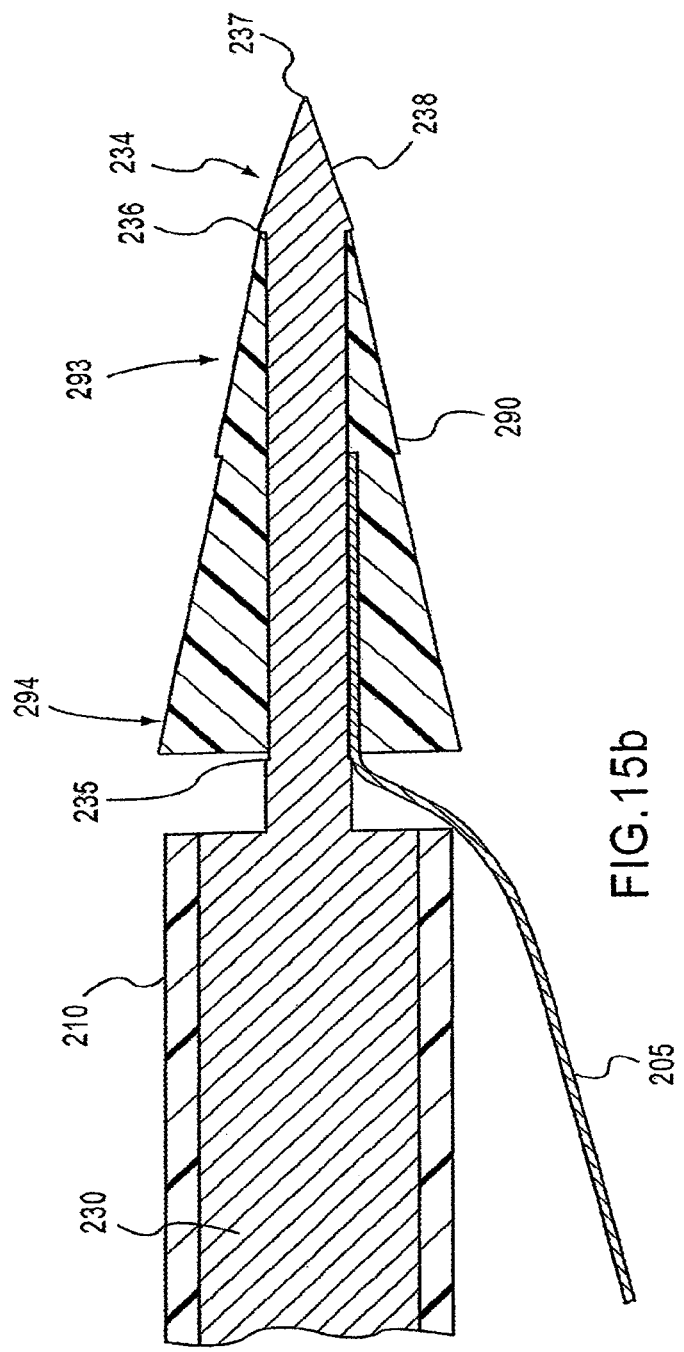
Figure 16:
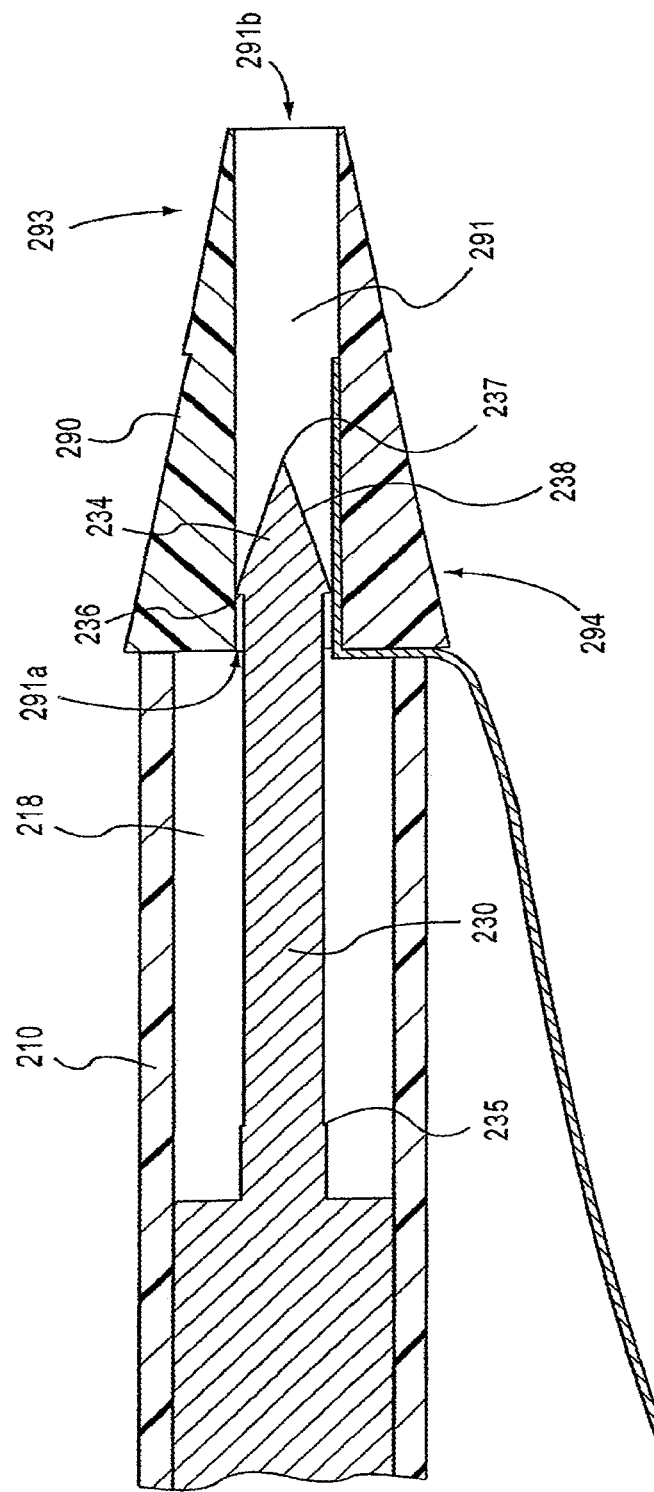
FIG. 16 is a cross-sectional view of a distal end portion of the insertion device of FIG. 6 in a second position along line Y-Y.

The stylet 230 includes a distal end portion 234 and a proximal end portion 232. The stylet 230 is slidably disposed within the lumen 218 defined by the elongate member 210. As shown in FIG. 13, the distal end portion 234 of the stylet 230 defines a first ridge 235, a second ridge 236, a tip 237, and a tapered portion 238 extending between the second ridge 236 and the tip 237. The tip 237 can be a variety of shapes, for example, in one embodiment, the stylet tip is pointed. In another embodiment, the stylet tip can be sharp. In yet another embodiment, the tip is blunt.

The distal end portion 234 of the stylet 230 is configured to extend through a lumen 291 (shown, for example in FIGS. 15a, 15b, 16, and 20) defined by the mesh carrier 290. The first ridge 235 is configured to interact with a proximal end portion 294 of the mesh carrier 290. The second ridge 236 is configured to be disposed outside of the lumen 291 and interact with a distal end portion 293 of the mesh carrier 290 (described in more detail below).

The proximal end portion 232 of the stylet 230 is slidably coupled to the elongate member 210 and extends through the lumen 218 of the elongate member 210. In the illustrated embodiment, the proximal end portion 232 includes detents 231a and 231b and a lip 233 (shown, for example, in FIGS. 7 and 8). The detents 231a are configured to mate with the projections 256, 257 of the base member 250 of the elongate member 210 when the stylet 230 is in its first position (shown in FIG. 11). The detents 231b and the lip 233 are configured to interact and/or contact the projections 256, 257 of the base member 250 when the stylet 230 is moved proximally from a first position to a second position (shown in FIG. 12).

As shown in FIG. 13, at least a portion of the stylet 230 defines a first diameter. A portion of the proximal end portion 232 defines a second diameter different from the first diameter of the distal end portion 234. In the illustrated embodiment, the second diameter is greater than the first diameter.

The proximal end portion 232 of the stylet 230 is coupled to a handle 270. The handle 270 includes a proximal end portion 272 and a distal end portion 274. As shown, for example, in FIGS. 3, 4a, and 5, the distal end portion 274 of the handle 270 is fixedly coupled to the proximal end portion 232 of the stylet. Thus movement of the handle in a proximal direction with respect to the elongate member 210 causes the stylet to move in a proximal direction, and movement in a distal direction with respect to the elongate member 210 causes the stylet to move in a distal direction.

The handle 270 can be coupled to the stylet 230 by any known coupling mechanism, including, but not limited to, a clip, adhesive, interference fit, mating recesses, or the like. In another embodiment, the handle is coupled to the delivery assembly by any combination of the foregoing known coupling mechanisms. In other embodiments, the handle and the stylet can be monolithically constructed. In yet other embodiments, for example, the handle can be insert-molded to the stylet.

Although the handle 270 is illustrated as defining a contoured shape (shown, for example, in FIGS. 2 and 3), the handle 270 can define a variety of shapes, sizes, and configurations, such as a cylindrical shape. The handle 270 can further be constructed of any suitable material. For example, in some embodiments, the handle 270 can be constructed of at least one polymer. In other embodiments, for example, the handle 270 can be constructed of acrylonitrile butadiene styrene (ABS). In other embodiments, the handle 270 can include a thermoplastic elastomer (TPE) material covering a portion its outer surface to provide a practitioner a comfortable or secure gripping area.

The stylet 230 has a first position (i.e., an extended position), shown, for example, in FIG. 2 and a second position (i.e., a retracted position), shown, for example, in FIG. 3. When the stylet 230 is in its first position, at least a portion of the distal end portion 234 of the stylet 230 extends from the lumen 218 at the distal end portion 213 of the elongate member 210.

The portion of the distal end portion 234 is further configured to extend through the lumen 291 and out an opening 291b defined by the mesh carrier 290. Specifically the stylet 230 is configured to extend through the lumen 291 and out of opening 291b of the mesh carrier 290 (as shown, for example, in FIGS. 6, 15a-16, and 20) such that the first ridge 235 interacts with the proximal end portion 294 of the mesh carrier 290, and the second ridge 236 defined by the distal end portion 234 of the stylet 230 interacts with distal end 293 of the mesh carrier 290. The interaction of the first ridge 235 and the second ridge 236 with the mesh carrier helps retain the mesh carrier 290 on the distal end portion 234 of the stylet 230. As the stylet 230 is moved from its first position to its second position, the distal end portion 213 of the elongate member 210 contacts the proximal end 294 of the mesh carrier 290 and prevents proximal movement of the mesh carrier 290. When the stylet 230 is in its second position, as illustrated, for example, in FIG. 3, the portion of the distal end portion 234 of the stylet 230, which was disposed outside the lumen 218 when the stylet 230 was its first position, is disposed within the lumen 218 of the elongate member 210. Specifically, in the illustrated embodiment, when the stylet 230 is moved proximally from its first position, the distal end portion 213 of the elongate member 210 contacts the proximal end 294 of the mesh carrier 290 maintaining its location within bodily tissue. The mesh carrier 290 is thereby decoupled or removed from the distal end portion 234 of the stylet 230 and is released in bodily tissue.

The stylet 230 can be constructed of any material suitable for insertion into a body of a patient. For example, in some embodiment, the stylet can be constructed of stainless steel. In other embodiments, the stylet can be constructed of a polymer.

Figure 17:
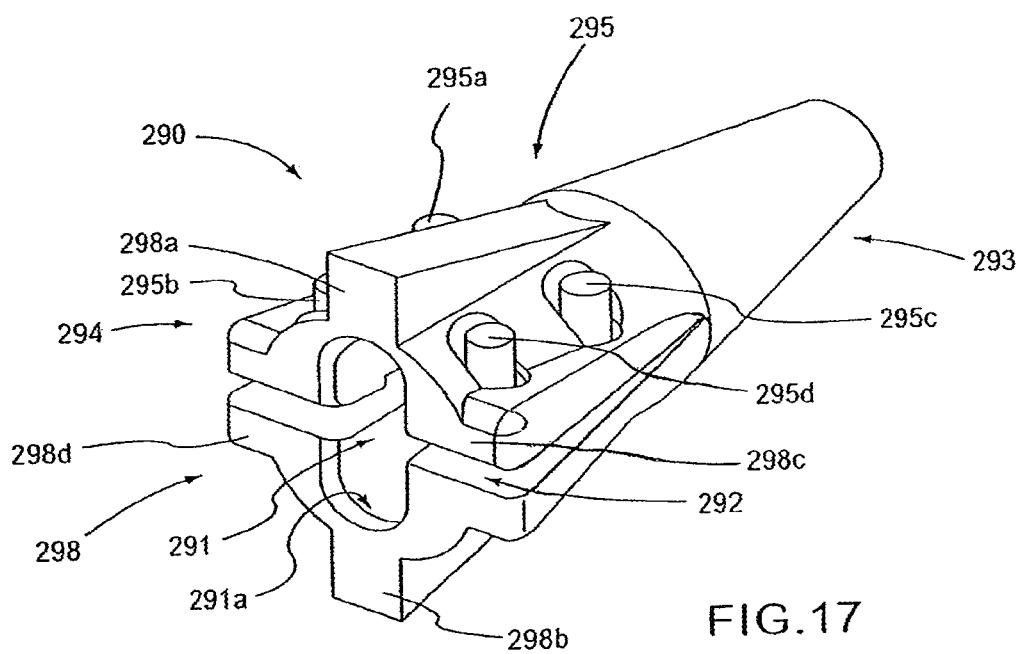
FIGS. 17 and 18 are perspective views of an embodiment of a mesh carrier.
Figure 18:
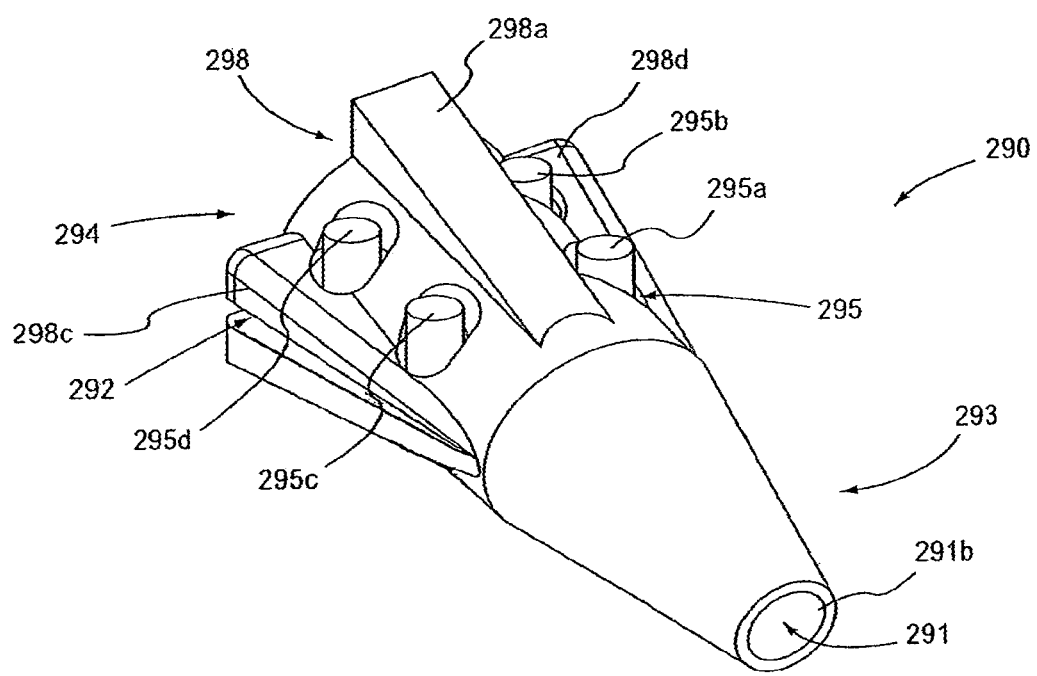

FIGS. 17 and 18 are perspective views of a mesh carrier 290 that can be used with the insertion device 200 described above. The mesh carrier 290 has a proximal end 294 and a distal end 293 and defines a lumen 291 extending from the proximal end 294 to the distal end 293. The mesh carrier 290 is removably coupled to the distal end portion 234 of the stylet 230, as shown, for example, in FIGS. 5, 6, 15a-16, and 20. The proximal end portion 294 defines an opening 291a in communication with the lumen 291. The opening 291a is configured to receive the distal end portion 234 of the stylet 230. The proximal end 294 of the mesh carrier 290 is proximate the distal end portion 213 of the elongate member 210 of the insertion device 200 when the stylet 230 is in its first position. The proximal end 294 contacts the distal end portion 213 while the stylet 230 is moved from its first position to its second position. Thus, by moving the stylet 230 in a proximal direction from its first position to its second position, the mesh carrier 290 is decoupled from the stylet 230, and fixed to bodily tissue.

The proximal end portion 294 of the mesh carrier 290 further includes a retention portion 295, an anchor portion 298 and defines an aperture 292. The retention portion 295 includes four projections 295a, 295b, 295c, and 295d extending therefrom. The retention portion 295 is configured to retain or secure at least a portion of a filament 205 with respect to the mesh carrier 290. Specifically, in the illustrated embodiment, the projections 295a-295d are configured to help prevent movement of the filament 205 with respect to the aperture 292 of the mesh carrier 290 when the mesh carrier 290 is placed into bodily tissue. The projections 295a-295d are configured such that when a portion of the filament 205 extends into the aperture 292, the projections 295a-295d pierce the filament 205 to secure the filament 205 within the aperture 292 of the mesh carrier 290. Thus, the filament 205 is retained in place with respect to the mesh carrier 290 by its interaction with the retention portion 295.

Although the retention portion 295 is illustrated and described as including four projections 295a-295b, in one embodiment, the retention portion 295 includes three projections. In another embodiment, the retention portion 295 includes one or two projections. Alternatively, the retention portion 295 can include five of more projections.

Although the retention portion 295 is illustrated as including projections 295a-295d configured to engage or secure a filament 205, in one embodiment, the retention portion 295 includes a different mechanism for retaining the filament 205 with respect to the mesh carrier 290. For example, in one embodiment, the retention portion 295 includes a clip, an adhesive or the like. In another embodiment, the retention portion 295 includes any combination of a projection, clip, adhesive, or the like.

The anchor portion 298 of the mesh carrier 290 is configured to help retain at least a portion of the mesh carrier 290 in a body of a patient. The anchor portion 298 is configured to help prevent the mesh carrier 290 from moving through the bodily tissue in which it is placed. For example, in one application, the anchor portion 298 is configured to retain or anchor the mesh carrier 290 in one of the obturator internus or obturator externus muscles. As illustrated in FIGS. 17 and 18, the anchor portion 298 is disposed on or proximate to the proximal end portion 294 of the mesh carrier 290. The anchor portion 298 includes protrusions 298a, 298b, 298c, and 298d. The protrusions 298a-298d are configured to help anchor the mesh carrier 290 in the bodily tissue of the patient once the mesh carrier 290 is placed within the bodily tissue.

In the embodiment illustrated in FIGS. 17 and 18, the protrusions 298a-298d are configured to extend outwardly from the mesh carrier 290 such that when the mesh carrier 290 is placed into bodily tissue and the insertion device is removed, bodily tissue may regress behind the mesh carrier 290, thus helping to anchor the mesh carrier 290 in the bodily tissue.

Figure 19:
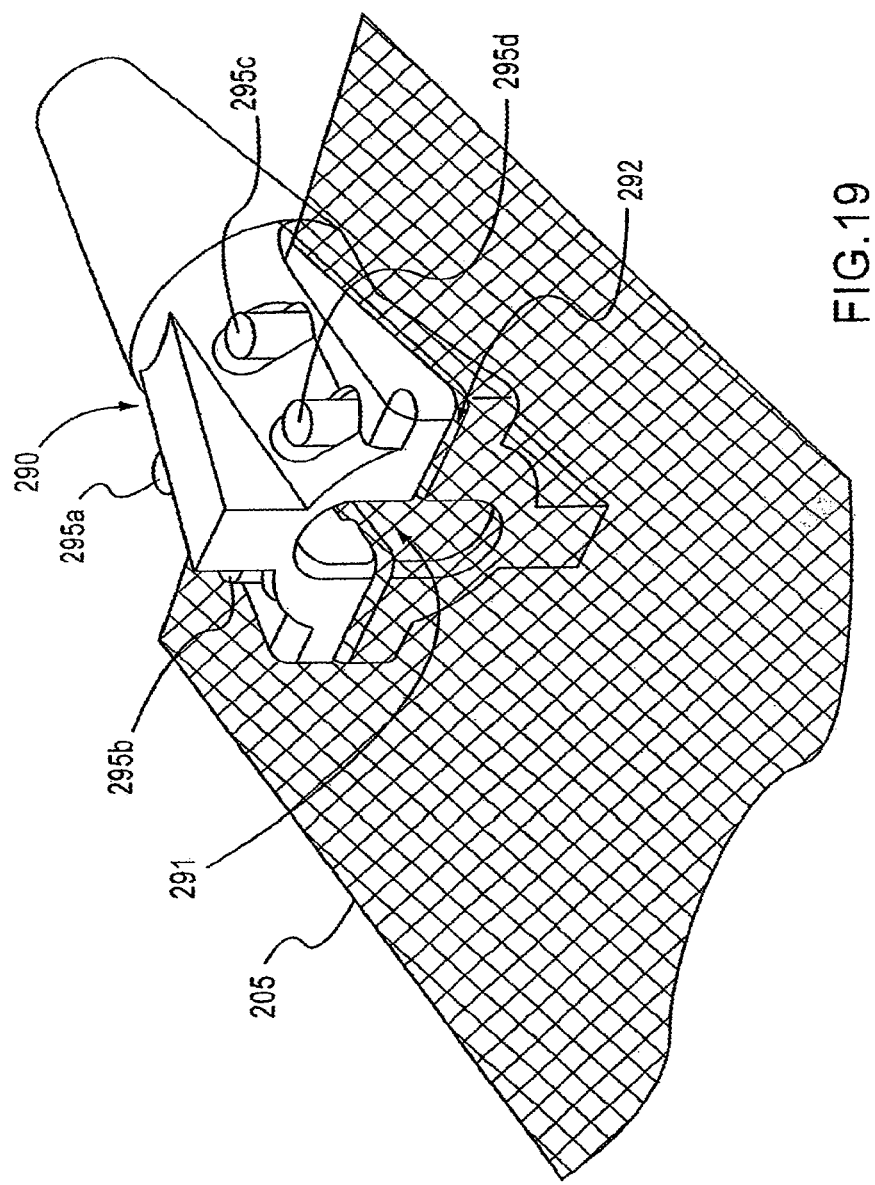
FIG. 19 is a perspective view of a mesh carrier and a filament according to an embodiment.
Figure 20:
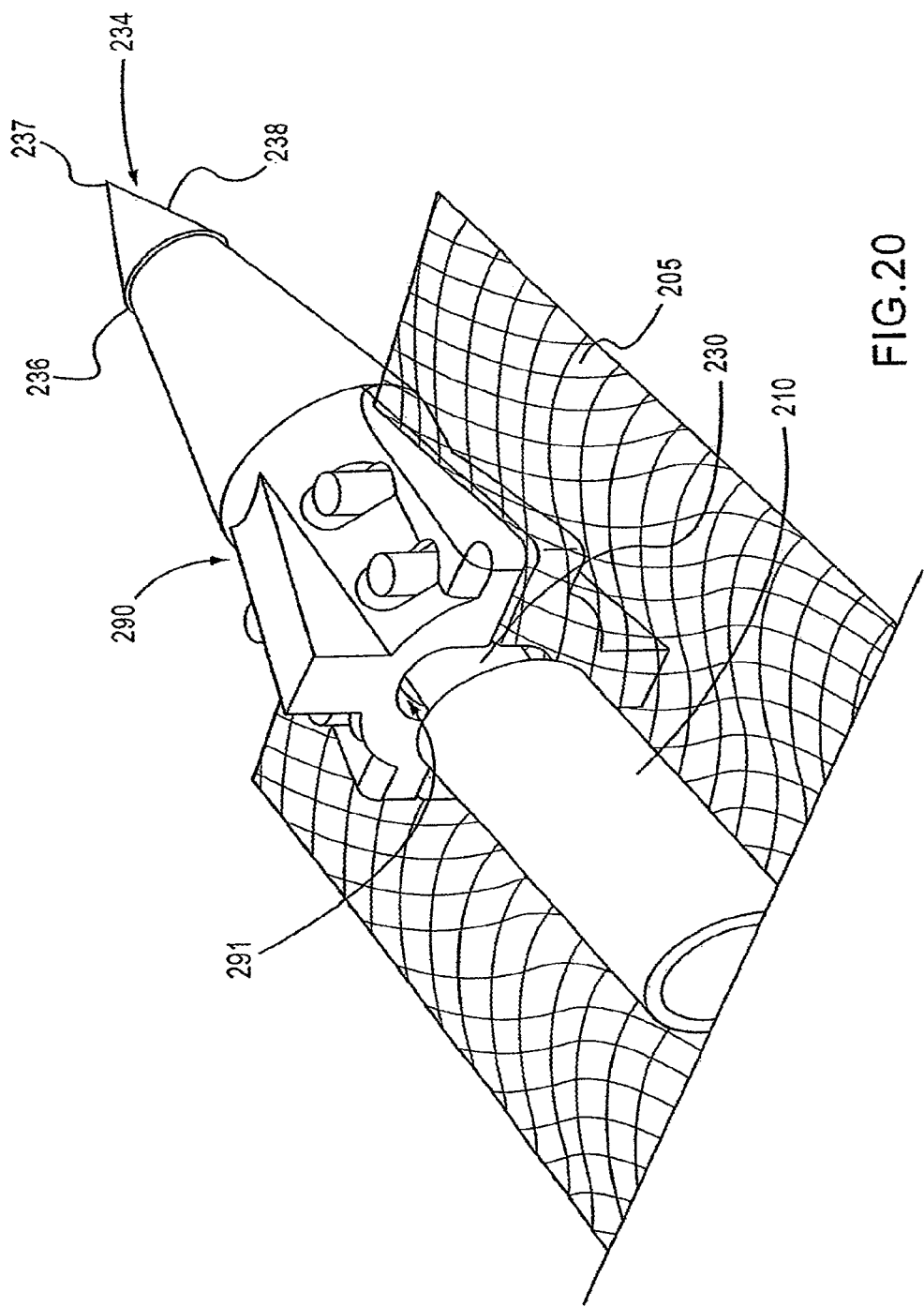
FIG. 20 is a perspective view of a portion of the insertion device of FIG. 6 coupled to a mesh carrier and a filament.

The aperture 292 is configured to receive at least a portion of the filament 205 (shown in FIGS. 19-21) such that the filament 205 is disposed adjacent to the stylet 230 (not shown). The aperture 292 can be configured to provide little or no resistance to movement or adjustment of the filament 205. For example, the aperture 292 can have an opening greater in size than the width or thickness of the filament 205. In such an embodiment, the filament 205 can be readily placed within aperture 292, meeting minimal or no resistance, before the filament 205 is pierced by the projections 295a-295d.

In another embodiment, the aperture 292 can be configured to provide a friction fit with the filament 205 passed through (or received within) the aperture 292. For example, the aperture 292 can be configured to be slightly less (or narrower) than the thickness of the filament 205. In such an embodiment, a force must be applied to move the filament 205 through the aperture 292. This configuration would allow the filament 205 to be further secured by the mesh carrier 290.

The aperture 292 can have any suitable size or shape configured to receive the filament 205, for example the shape can be a U-shape, square, rectangle, or any other shape configured to receive a filament 205.

The mesh carrier 290 can be constructed of any material suitable for implantation into bodily tissue. For example, the mesh carrier 290 can be constructed of implantable grade polypropylene, implantable grade metal, a polymer, a biocompatible material, or any combination thereof. Suitable biocompatible materials include bioabsorbable, cadaveric, and bovine materials.

Figure 21:
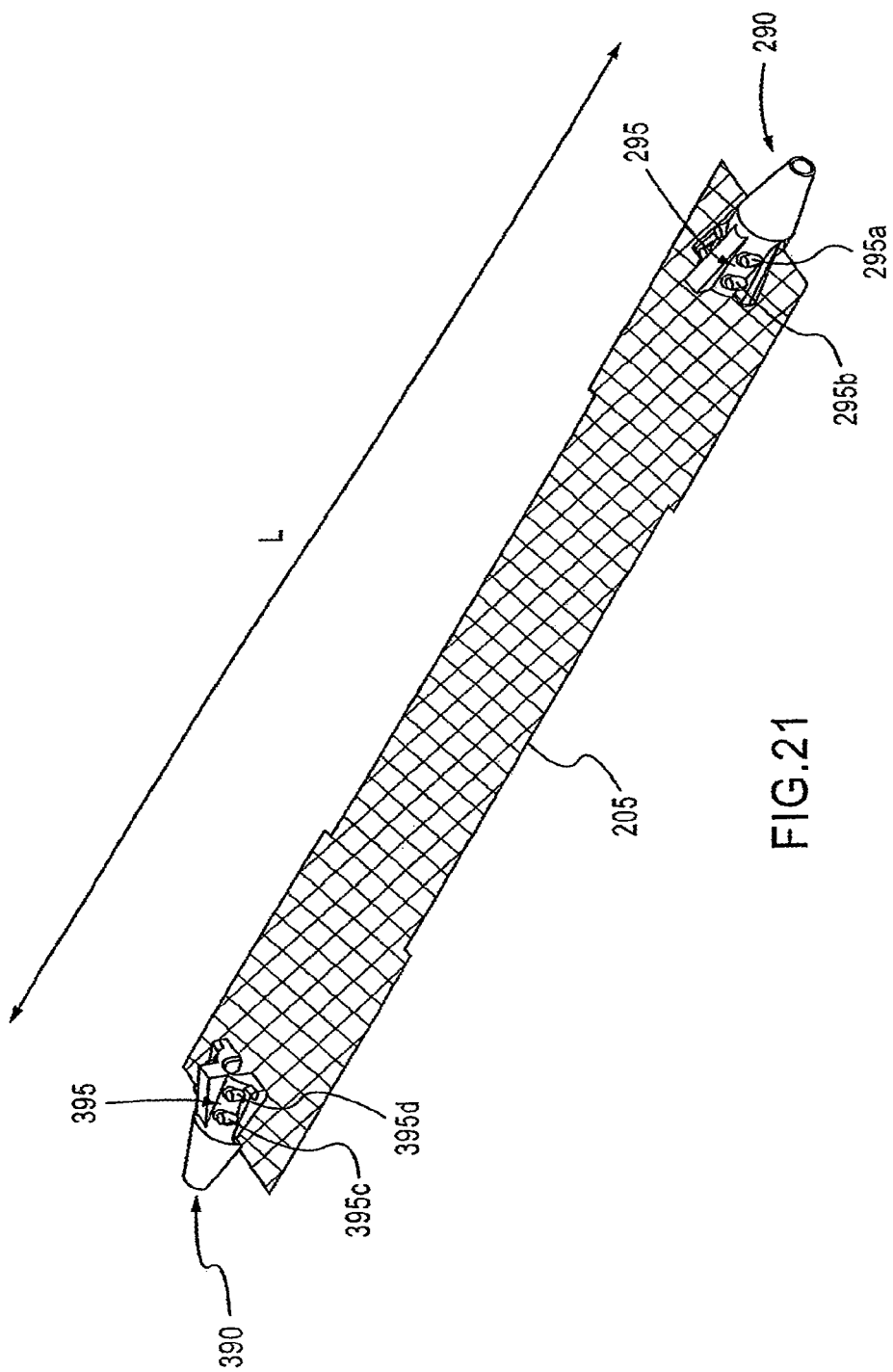
FIG. 21 is a perspective view of two mesh carriers and a filament according another embodiment.

In some embodiments, the mesh earner 290 can be preassembled with the filament 205 at a manufacturing facility. The preassembled set can include two mesh carriers 290 and 390 and a filament 205 of a specified or known length. For example, as shown in FIG. 21, a first end portion 205a of the filament 205 can be inserted and secured with respect to a first mesh carrier 290 at the manufacturing facility. Additionally, a second end portion 205b of the filament 205 can be inserted and secured with respect to a second mesh carrier 390. Specifically, in the illustrated embodiment, the first end portion 205a of the filament 205 is pierced by the projections 295a and 295b (others not shown) of the first mesh carrier 290 thereby retaining the first end portion 205a of the filament 205 within the retention portion 295 of the first mesh carrier 290. The second end portion 205b of the filament 205 is pierced by the projections 395c and 395d (others, not shown) of the second mesh carrier 390 thereby retaining the second end portion 205a of filament 205 within the retention portion 395 of the second mesh carrier 390. The filament 205 extends between the first mesh carrier 290 and the second mesh carrier 390 creating a fixed length L of filament 205.

The filament 205 as discussed above can be constructed of many different suitable materials and have many different suitable configurations. For example, in some embodiments, a polymer mesh implant can be used, which can be used to support the urethra. In other embodiments, a polyform material can be used.

In some embodiments, at least a portion of the filament can be reinforced, such as with a reinforcing material. The reinforcing material, or reinforced portion of the filament, can be configured to assist in suspending or supporting the bodily tissue or organ. In one embodiment, the filament can be reinforced by a suture.

In some embodiments, at least a portion of the filament can include tangs or a tanged portion to grip or attach to a portion of bodily tissue. The terms "tanged" or "tangs" as used herein mean roughened or jagged edges or areas, such as can result from cutting a woven or knit mesh material or filament. The tangs enhance anchoring of the filament within bodily tissue, such as pubo-urethral tissue. In one embodiment, the filament includes tangs on an edge along an entire length of the filament. In another embodiment, tangs are only on the end portions of the filament.

In other embodiments, the filament can be untanged, or detanged, such as by heating the tangs on a polymer mesh so that they fuse and bead up to form a smooth finish.

In some embodiments, the filament can include a coating. For example, the filament can include a polymeric coating. In another example, the filament can include a therapeutic agent coating.

In some embodiments, the filament can be porous. A porous filament defines openings, or pores, in the filament or between threads of material forming the filament. For example, in one embodiment, the filament is a mesh. The filament can be a micro-porous mesh in which the openings, or pores, are small.

FIG. 21 illustrates an example of the first mesh carrier 290 and the second mesh carrier 390 anchored in bodily tissue T of the pelvic region of a patient. A first end portion 205a of a filament 205 is retained by the first mesh carrier 290 and a second end portion 205b of the filament 205 is retained by the second mesh carrier 390. Specifically, the filament 205 extends between the first mesh carrier 290 and the second mesh carrier 390 to provide support to the target tissue T or organ, such as the urethra.

Figure 23:
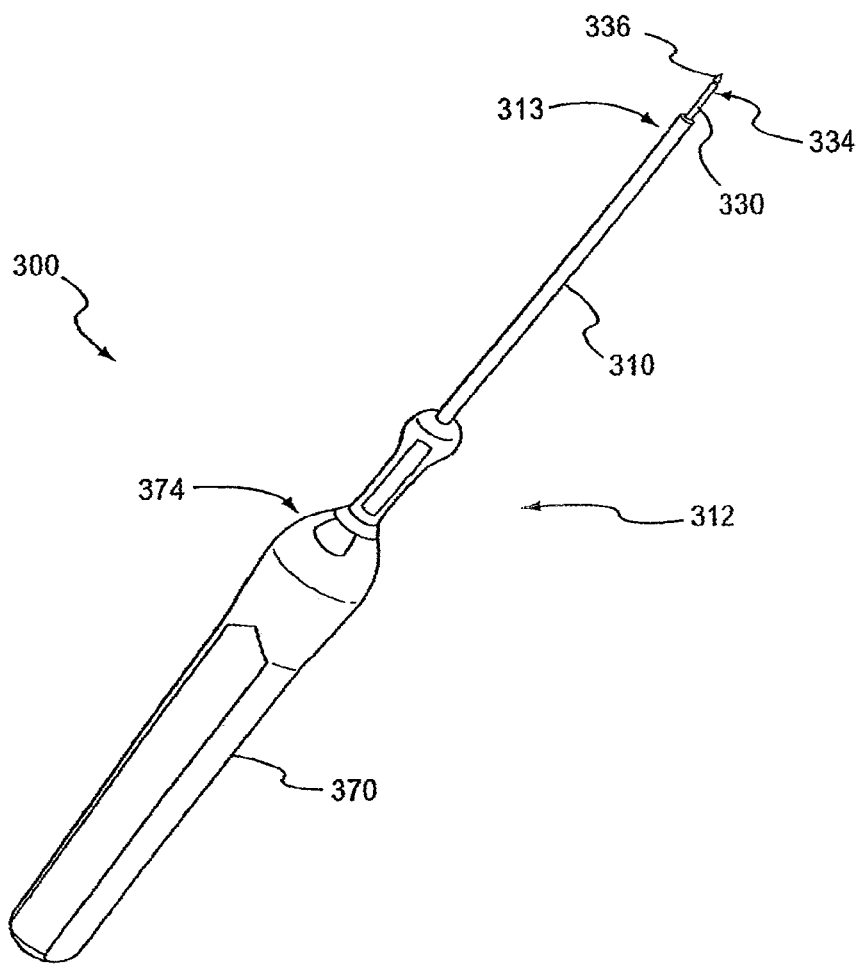
FIG. 23 is a perspective view of an insertion device with a stylet in a first position according to another embodiment.
Figure 24:
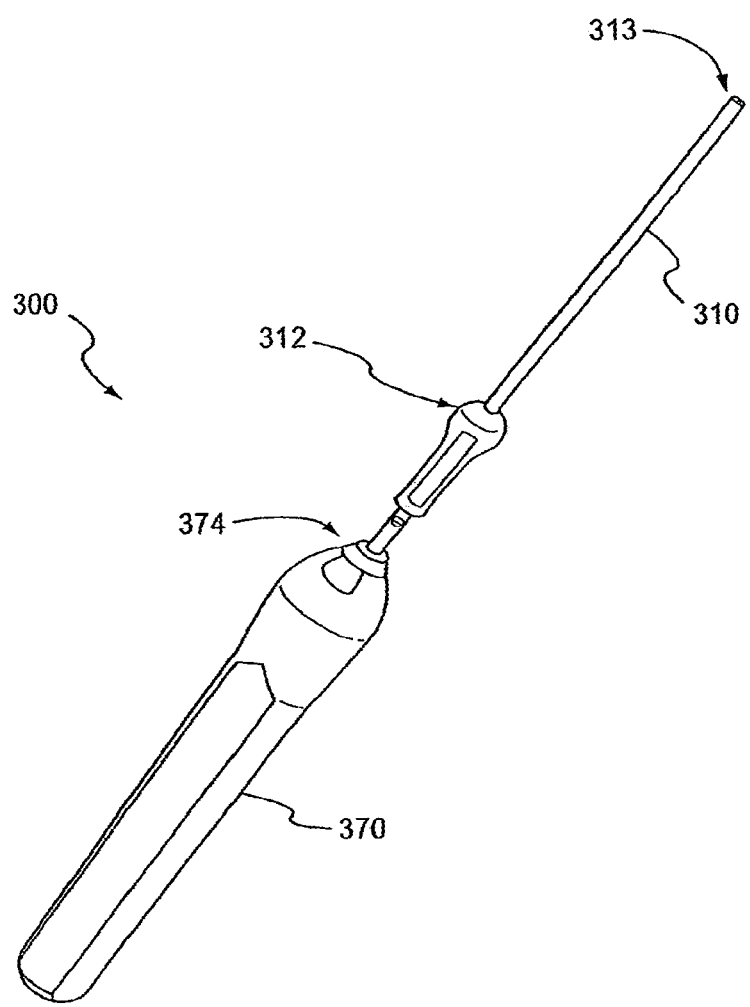
FIG. 24 is a perspective view of the insertion device of FIG. 23 with the stylet in a second position.

Although the stylet 230 as illustrated in FIGS. 2-6 has a curved configuration, it should be understood that other configurations are possible. As shown, for example in FIGS. 23 and 24, stylet 330 can have a substantially straight, or linear, configuration. In such embodiments, a portion of the distal end portion 334 is configured to extend through the mesh carrier (not shown). Specifically, the stylet 330 is configured to extend through the lumen and out of the opening of the mesh carrier such that the second ridge 336 defined by the distal end portion 334 of the stylet 330 interacts with distal end of the mesh carrier and helps retain the mesh carrier on the distal end portion 334 of the stylet 330. As the stylet 330 is moved from its first position to its second position, the distal end portion 313 of the elongate member 310 contacts the proximal end of the mesh carrier and prevents proximal movement of the mesh carrier. When the stylet 330 is in its second position, as illustrated, for example, in FIG. 24, at least a portion of the distal end portion 334 of the stylet 330 is disposed within the lumen of the elongate member 310. Specifically, in the illustrated embodiment, when the stylet 330 is moved proximally from its first position, the distal end portion 313 of the elongate member 310 contacts the proximal end of the mesh carrier maintaining its location within bodily tissue. The mesh carrier is thereby decoupled or removed from the distal end portion 334 of the stylet 330 and is released in bodily tissue.

Further examples of such insertion devices with stylets having linear configurations are described in U.S. Publication No. 2006/0089524 to Chu and U.S. Publication No. 2007/0015953 to MacLean. The disclosures of U.S. Publication Nos. 2006/0089524 and 2007/0015953 are incorporated herein by reference in their entirety. Additional variations in size, shape, and configurations are also described in the above noted publications.

Figure 25:
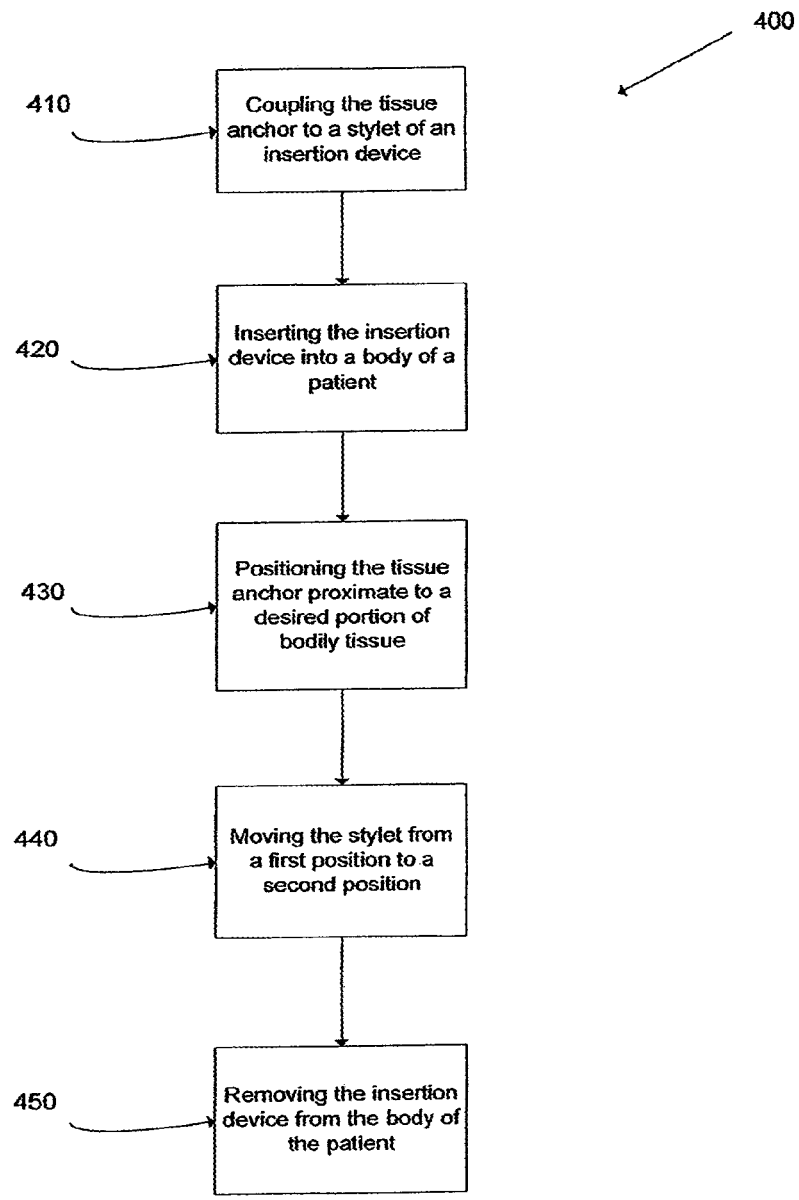
FIG. 25 is a flowchart of a method according to an embodiment of the invention.

FIG. 25 is a flowchart of a method 400 for delivering a mesh carrier into bodily tissue of a patient using an insertion device according to an embodiment of the invention.

At 410, the mesh carrier is coupled to the stylet of the insertion device. For example, the distal end portion of the mesh carrier is engaged with the distal end portion of the stylet.

In some embodiments, at least a portion of a filament is inserted into the aperture defined by the mesh carrier prior to the coupling of the mesh carrier to the stylet.

In some embodiments, the mesh carrier is coupled to or engaged with the distal end portion of the stylet when the stylet is in its first position. In such an embodiment, the distal end portion of the stylet extends through the lumen defined by the mesh carrier and is disposed adjacent the filament retained in the retention portion (e.g., projections) of the mesh earner.

At 420, the insertion device is inserted into a body of a patient. For example, in one embodiment, the insertion device is inserted into the body of the patient through an incision made in bodily tissue. In a procedure for urinary incontinence, a transvaginal approach may be used to insert the delivery instrument into the body of the patient.

At 430, the mesh carrier is positioned proximate to a desired portion of bodily tissue, and, the mesh carrier is inserted into the bodily tissue. For example, in a procedure for female urinary incontinence, the mesh carrier is inserted into one of the obturator internus or obturator externus muscles. In one embodiment, an anterior vaginal incision is made, and the mesh carrier is inserted into the bodily tissue through such incision.

At 440, the stylet is moved from its first position to its second position. Specifically, in the illustrated embodiment, the stylet is moved in a proximal direction, from its first position to its second position, so that the distal end portion of the stylet is withdrawn from the lumen of the mesh carrier. By withdrawing the distal end portion of the stylet from the lumen of the mesh carrier and disposing the distal end portion within the lumen of the elongate member, the distal end portion of the elongate member contacts the proximal end portion of the mesh carrier thereby maintaining the mesh carrier's position within the bodily tissue as the stylet is removed from the lumen of the mesh carrier. Thus, the mesh carrier is decoupled or removed from the stylet thereby fixing the mesh carrier and filament within the bodily tissue. For example, in one procedure, a practitioner concurrently pulls the handle of the elongate member in a proximal direction while holding the base member of the elongate member substantially stationary.

In some embodiments, the elongate member is moved from a first position to a second position while maintaining the stylet substantially stationary. The elongate member moves relative to the stylet, in a distal direction, from a first position to a second position, such that the distal end portion of the elongate member contacts the proximal end portion of the mesh carrier to decouple the mesh carrier from the stylet. For example, in one procedure, a practitioner concurrently holds the handle of the stylet substantially stationary while pushing the base member of the elongate member in the distal direction to move the elongate member to its second position.

At 450, the insertion device is withdrawn from the body of the patient.

Although the method of delivering a mesh carrier into bodily tissue has been illustrated and described in one order, the activities can occur in a different order. For example, in some embodiments, the mesh carrier is engaged with the stylet of the insertion device prior to inserting the filament into the aperture defined by the mesh carrier.

Figure 22:
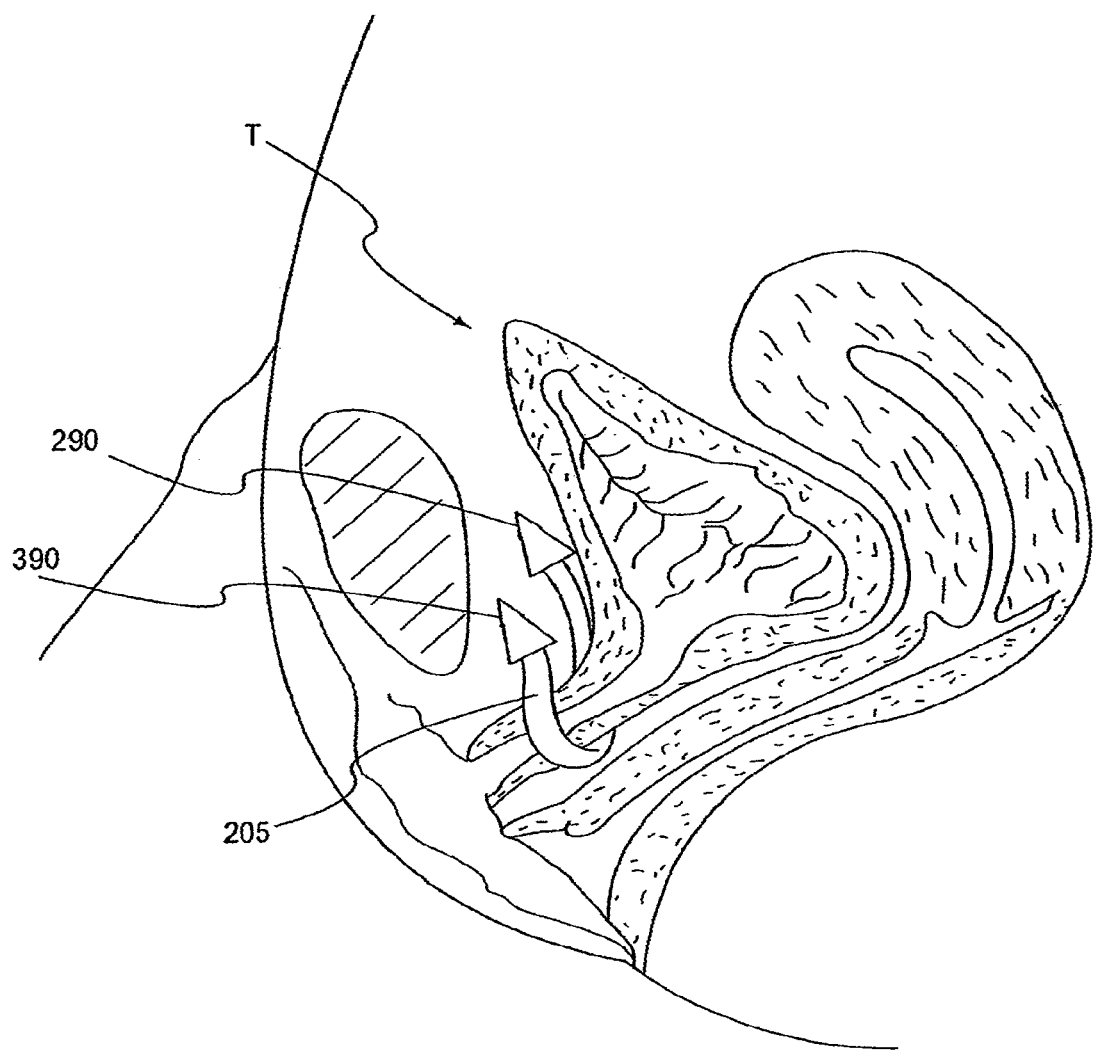
FIG. 22 is a side view of an embodiment of an implant shown positioned within a body of a patient.

A method for delivering a mesh carrier into bodily tissue of a patient can include delivering more than one mesh carrier for securing a filament to bodily tissue. For example, in one embodiment, as illustrated in FIG. 22, two mesh carriers are delivered into bodily tissue of the patient.

Alternatively, three, four, or more mesh carriers can be delivered into bodily tissue of the patient. In an embodiment with two or more mesh carriers, the first mesh carrier is delivered as described above. The tension of the filament can be adjusted by inserting the second mesh carrier to a specific location within the patient.

In one embodiment, an insertion device includes an elongate member and a stylet. The elongate member has a proximal end portion, a distal end portion, and defines a lumen therethrough. The stylet has a distal end portion, a proximal end portion, and is slidably coupled to the elongate member. The stylet is configured to move from a first position to a second position with respect to the elongate member. The distal end portion of the stylet is configured to removably couple a mesh carrier thereto. A portion of the distal end portion of the stylet is disposed outside of the lumen of the elongate member when the stylet is in its first position and is disposed within the lumen when the stylet is in its second position.

In some embodiments, the stylet includes a curved portion. The distal end portion of the stylet has a first diameter and the proximal end portion of the stylet has a second diameter. The second diameter is greater than the first diameter. The distal end portion of the stylet defines a ridge, a tip, and a tapered portion extending between the ridge and the tip. The ridge is configured to interact with the mesh carrier and is configured to be disposed outside of and contact a distal end portion of the mesh carrier. The distal end portion of the stylet is configured to extend through a lumen defined by the mesh carrier and extend outside of a distal end portion of the mesh carrier.

In some embodiments, the proximal end portion of the elongate member includes a base portion having at least one protrusion. The proximal end portion of the stylet includes a stopping portion configured to engage the at least one protrusion of the base portion. The proximal end portion of the stylet includes a stopping portion having lip. The lip is configured to engage a protrusion of the elongate member when the stylet is moved from its first position to its second position.

In some embodiments, the insertion device includes a handle coupled to the stylet. The proximal end portion of the elongate member is configured to contact a distal end portion of the handle when the stylet is in its first position and is configured to be spaced apart from the distal end portion of the handle when the stylet is in its second position.

In some embodiments, the distal end portion of the elongate member is configured to contact the mesh carrier when the stylet is moved from its first position to its second position. The distal end portion of the elongate member is configured to contact a proximal end portion of the mesh carrier to decouple the mesh carrier from the stylet when the stylet is moved from its first position to its second position.

In some embodiments, the stylet includes stainless steel.

In another embodiment, an insertion device includes an elongate member and a stylet. The elongate member has a proximal end portion, a distal end portion, and defines a lumen therethrough. The stylet has a distal end portion and a proximal end portion and is configured to move from a first position to a second position. The distal end portion of the stylet is configured to removably couple a mesh carrier thereto. The distal end portion of the stylet is coupled to the mesh carrier when the stylet is in its first position. The elongate member is configured to contact the mesh carrier and decouple the mesh carrier from the distal end portion of the stylet when the stylet is moved from its first position to its second position.

In some embodiments, the distal end portion of the elongate member is configured to contact a proximal end portion of a mesh carrier when the stylet is in its first position. The distal end portion of the stylet defines a ridge, a tip, and a tapered portion extending between the ridge and the tip, the ridge being configured to interact with the mesh carrier. The proximal end portion of the elongate member includes a base portion. The base portion has at least one protrusion. The stylet has a stopping portion configured to engage the at least one protrusion of the base portion.

In yet another embodiment, a mesh carrier has a proximal end portion, a distal end portion, and defines a lumen between the proximal end portion and the distal end portion. The proximal end portion defines an aperture configured to receive a portion of a filament therein. The proximal end portion includes a retention portion to secure the portion of the filament with respect to the mesh carrier. The lumen is configured to receive a stylet therein wherein the stylet is disposed adjacent the filament. The distal end portion of the mesh carrier is configured to interact with the stylet.

In some embodiments, the retention portion of the proximal end portion of the mesh carrier includes projections configured to pierce the portion of the filament.

In some embodiments, the mesh carrier includes an anchor portion configured to anchor the mesh carrier in a bodily tissue of a patient.

In another embodiment, a method includes coupling a mesh carrier to a distal end portion of a stylet of an insertion device, wherein the stylet is movably coupled to an elongate member, inserting the insertion device into a body of a patient, moving the stylet with respect to the elongate member from a first position to a second position to decouple the mesh carrier from the stylet of the insertion device; and removing the insertion device from the body.

In some embodiments, the coupling of the mesh carrier includes moving the stylet to its first position such that a distal end portion of the stylet extends beyond a distal end portion of the elongate member. The coupling of the mesh carrier also includes inserting the stylet into a lumen defined by the mesh carrier such that a ridge defined by the distal end of the stylet interacts with the mesh carrier.

In some embodiments, the moving of the stylet to its second position includes moving the stylet in a distal direction.

In some embodiments, the method includes coupling a second mesh carrier to a distal end portion of the stylet and inserting the insertion device into the body of the patient, moving the stylet with respect to the elongate member from its first position to its second position to decouple the second mesh carrier from the insertion device, and removing the insertion device from the body.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The previous description of the embodiments is provided to enable any person skilled in the art to make or use the invention. While the invention has been particularly shown and described with reference to embodiments thereof, it will be understood by those skilled in art that various changes in form and details may be made. For example, a delivery instrument can include various combinations and sub-combinations of the various embodiments described herein.

What is claimed is:

1. An insertion device, comprising:
an elongate member having a proximal end portion, a distal end portion, and defining a lumen therethrough; and
a stylet having a distal end portion, a proximal end portion, and being slidably coupled to the elongate member, the stylet being configured to move from a first position to a second position with respect to the elongate member, the distal end portion of the stylet being configured to removably couple a tissue anchor thereto, the distal end portion of the stylet defines a ridge configured to be disposed outside of and contact an exterior surface of a distal end portion of the tissue anchor, a portion of the distal end portion of the stylet being disposed outside of the lumen of the elongate member when the stylet is in its first position, the portion of the distal end portion of the stylet being disposed within the lumen when the stylet is in its second position.

2. The insertion device of claim 1, wherein the stylet includes a curved portion.

3. The insertion device of claim 1, wherein the distal end portion of the stylet has a first diameter and the proximal end portion of the stylet has a second diameter, wherein the second diameter is greater than the first diameter.

4. The insertion device of claim 1, wherein the distal end portion of the stylet defines a tapered portion extending between the ridge and the tip.

5. The insertion device of claim 1, wherein the distal end portion of the stylet is configured to extend through a lumen defined by the tissue anchor.

6. The insertion device of claim 1, wherein the proximal end portion of the elongate member includes a base portion having at least one protrusion, the proximal end of the stylet having a stopping portion configured to engage the at least one protrusion of the base portion.

7. The insertion device of claim 1, wherein the proximal end portion of the stylet includes a stopping portion having lip, the lip configured to engage a protrusion of the elongate member when the stylet is moved from its first position to its second position.

8. The insertion device of claim 1, wherein the distal end portion of the elongate member is configured to contact the tissue anchor when the stylet is moved from its first position to its second position.

9. The insertion device of claim 1, wherein the distal end portion of the elongate member is configured to contact a proximal end portion of the tissue anchor to decouple the tissue anchor from the stylet when the stylet is moved from its first position to its second position.

10. An insertion device comprising:
an elongate member having a proximal end portion, a distal end portion, and defining a lumen therethrough;
a stylet having a distal end portion and a proximal end portion, and being configured to move from a first position to a second position, the distal end portion being configured to removably couple a tissue anchor thereto, the distal end portion being coupled to the tissue anchor when the stylet is in its first position, the elongate member being configured to contact the tissue anchor and decouple the tissue anchor from the distal end portion of the stylet when the stylet is moved from its first position to its second position, the distal end portion of the stylet defines a ridge, a tip, and a tapered portion extending between the ridge and the tip, the ridge being configured to interact with the tissue anchor.

11. An insertion device, comprising:
an elongate member having a proximal end portion, a distal end portion, and defining a lumen therethrough; and
a stylet having a distal end portion, a proximal end portion, and being slidably coupled to the elongate member, the stylet being configured to move from a first position to a second position with respect to the elongate member, the distal end portion of the stylet being configured to removably couple a mesh carrier thereto and being configured to contact an exterior surface of the mesh carrier, a portion of the distal end portion of the stylet being disposed outside of the lumen of the elongate member when the stylet is in its first position, the portion of the distal end portion of the stylet being disposed within the lumen when the stylet is in its second position, the distal end portion of the elongate member being configured to contact a proximal end portion of the mesh carrier to decouple the mesh carrier from the stylet when the stylet is moved from its first position to its second position.

12. The insertion device of claim 11, wherein the mesh carrier is a tissue anchor.

13. The insertion device of claim 11, wherein the distal end portion of the stylet has a first diameter and the proximal end portion of the stylet has a second diameter, wherein the second diameter is greater than the first diameter.

14. The insertion device of claim 11, wherein the distal end portion of the stylet defines a ridge, a tip, and a tapered portion extending between the ridge and the tip, the ridge being configured to interact with the mesh carrier.

15. The insertion device of claim 11, wherein the distal end portion of the stylet is configured to extend through a lumen defined by the mesh carrier.

16. The insertion device of claim 11, wherein the distal end portion of the stylet is configured to extend outside of a distal end portion of the mesh carrier.

17. The insertion device of claim 11, wherein the proximal end portion of the elongate member includes a base portion having at least one protrusion, the proximal end of the stylet having a stopping portion configured to engage the at least one protrusion of the base portion.

18. The insertion device of claim 11, wherein the proximal end portion of the stylet includes a stopping portion having lip, the lip configured to engage a protrusion of the elongate member when the stylet is moved from its first position to its second position.

* * * * *